(12) United States Patent
Nakata

(10) Patent No.: US 9,116,127 B2
(45) Date of Patent: Aug. 25, 2015

(54) QUANTITATIVE DETERMINATION METHOD FOR TARGET PARTICLES, PHOTOMETRIC ANALYSIS DEVICE, AND COMPUTER PROGRAM FOR PHOTOMETRIC ANALYSIS

(71) Applicant: OLYMPUS CORPORATION, Tokyo (JP)

(72) Inventor: Hidetaka Nakata, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 28 days.

(21) Appl. No.: 14/045,002

(22) Filed: Oct. 3, 2013

(65) Prior Publication Data

US 2014/0099630 A1    Apr. 10, 2014

Related U.S. Application Data

(63) Continuation of application No. PCT/JP2012/060487, filed on Apr. 18, 2012.

(30) Foreign Application Priority Data

Apr. 18, 2011    (JP) .................................. 2011-092168

(51) Int. Cl.
*G01N 21/00*    (2006.01)
*G01N 21/76*    (2006.01)
(Continued)

(52) U.S. Cl.
CPC .............. *G01N 21/76* (2013.01); *C12Q 1/6818* (2013.01); *G01N 21/6428* (2013.01);
(Continued)

(58) Field of Classification Search
USPC ........... 356/335–343, 432–440, 243.1–243.8; 250/459.1, 458.1; 435/6.11, 5, 7.1
See application file for complete search history.

(56) References Cited

U.S. PATENT DOCUMENTS 4,251,733 A    2/1981    Hirleman, Jr.
5,308,990 A    5/1994    Takahashi et al.
(Continued)

FOREIGN PATENT DOCUMENTS

EP    1 906 172 A1    4/2008
JP    04-337446 A    11/1992
(Continued)

OTHER PUBLICATIONS

Park, Mira et al., "Counting the Number of Fluorophores Labeled in Biomolecules by Observing the Fluorescence-Intensity Transient of a Single Molecule" Bulletin of the Chemical Society of Japan, dated Aug. 30, 2005, vol. 78, No. 9, p. 1612-1618.
(Continued)

*Primary Examiner* — Hoa Pham
(74) *Attorney, Agent, or Firm* — Westerman, Hattori, Daniels & Adrian, LLP

(57) ABSTRACT

The method of the present invention includes: preparing a sample solution containing the target particles and luminescent probes to be bound to the target particles, and binding these in the sample solution; moving a position of a light detection region of the optical system in the sample solution using a confocal microscope or a multiphoton microscope, and detecting light signal emitted from the luminescent probe in the light detection region while moving the position of the light detection region, and individually detecting the target particles directly or indirectly; and counting the number of the detected target particles, and calculating the concentration of the target particles in the sample solution from the number of the counted target particles on the basis of a calibration curve that approximates the correlation between the concentration or quantity of the target particles in the sample solution and the number of the target particles.

20 Claims, 11 Drawing Sheets

(51) Int. Cl.
  *G01N 21/64* (2006.01)
  *C12Q 1/68* (2006.01)
(52) U.S. Cl.
  CPC ... *G01N 21/6458* (2013.01); *G01N 2021/6419* (2013.01); *G01N 2021/6421* (2013.01); *G01N 2021/6432* (2013.01); *G01N 2021/6441* (2013.01)

(56) References Cited

U.S. PATENT DOCUMENTS

| | | | |
|---|---|---|---|
| 5,866,336 | A | 2/1999 | Nazarenko et al. |
| 6,280,960 | B1 | 8/2001 | Carr |
| 6,376,843 | B1 | 4/2002 | Palo |
| 6,388,746 | B1 | 5/2002 | Eriksson et al. |
| 6,388,788 | B1 | 5/2002 | Harris et al. |
| 6,400,487 | B1 | 6/2002 | Harris et al. |
| 6,403,338 | B1 | 6/2002 | Knapp et al. |
| 6,710,871 | B1 | 3/2004 | Goix |
| 6,782,297 | B2 | 8/2004 | Tabor |
| 6,856,391 | B2 | 2/2005 | Garab et al. |
| 6,927,401 | B1 | 8/2005 | Palo |
| 8,284,484 | B2 | 10/2012 | Hoult et al. |
| 8,900,812 | B2 * | 12/2014 | Nishikawa et al. ........ 435/6.11 |
| 8,911,944 | B2 * | 12/2014 | Nakata et al. ............. 435/6.11 |
| 2001/0035954 | A1 | 11/2001 | Rahn et al. |
| 2002/0008211 | A1 | 1/2002 | Kask |
| 2002/0036775 | A1 | 3/2002 | Wolleschensky et al. |
| 2003/0036855 | A1 | 2/2003 | Harris et al. |
| 2003/0218746 | A1 | 11/2003 | Sampas |
| 2004/0022684 | A1 | 2/2004 | Heinze et al. |
| 2004/0051051 | A1 | 3/2004 | Kato et al. |
| 2004/0150880 | A1 | 8/2004 | Nakata et al. |
| 2005/0260660 | A1 | 11/2005 | van Dongen et al. |
| 2006/0078998 | A1 | 4/2006 | Puskas et al. |
| 2006/0158721 | A1 | 7/2006 | Nakata et al. |
| 2006/0256338 | A1 | 11/2006 | Gratton et al. |
| 2007/0231808 | A1 | 10/2007 | Gouda et al. |
| 2008/0052009 | A1 | 2/2008 | Chiu et al. |
| 2009/0159812 | A1 | 6/2009 | Livingston |
| 2010/0033718 | A1 | 2/2010 | Tanaami |
| 2010/0177190 | A1 | 7/2010 | Chiang et al. |
| 2010/0202043 | A1 | 8/2010 | Ujike |
| 2012/0318956 | A1 * | 12/2012 | Yamaguchi et al. ....... 250/203.3 |
| 2012/0319009 | A1 * | 12/2012 | Yamaguchi et al. ....... 250/459.1 |
| 2013/0048875 | A1 * | 2/2013 | Yamaguchi et al. ....... 250/459.1 |
| 2013/0122488 | A1 * | 5/2013 | Tanabe et al. ................ 435/5 |
| 2013/0230874 | A1 * | 9/2013 | Hanashi et al. ............. 435/15 |
| 2014/0004518 | A1 * | 1/2014 | Nakata et al. ............. 435/6.11 |
| 2014/0004519 | A1 * | 1/2014 | Nishikawa et al. ......... 435/6.11 |
| 2014/0131593 | A1 * | 5/2014 | Nakata et al. ............. 250/459.1 |
| 2014/0175262 | A1 * | 6/2014 | Nakata et al. ............... 250/206 |
| 2014/0329709 | A1 * | 11/2014 | Nakata ......................... 506/9 |

FOREIGN PATENT DOCUMENTS

| | | |
|---|---|---|
| JP | 2002-507762 A | 3/2002 |
| JP | 2002-543414 A | 12/2002 |
| JP | 2004-506192 A | 2/2004 |
| JP | 2005-098876 A | 4/2005 |
| JP | 2005-099662 A | 4/2005 |
| JP | 2006-333739 A | 12/2006 |
| JP | 2007-006890 A | 1/2007 |
| JP | 2007-020565 A | 2/2007 |
| JP | 4023523 B2 | 12/2007 |
| JP | 2008-116440 A | 5/2008 |
| JP | 2008-536093 A | 9/2008 |
| JP | 2008-292371 A | 12/2008 |
| JP | 2009-145242 A | 7/2009 |
| JP | 2009-281831 A | 12/2009 |
| JP | 2009-288161 A | 12/2009 |
| JP | 2010-190730 A | 9/2010 |
| JP | 2011-002415 A | 1/2011 |
| JP | 2011-036150 A | 2/2011 |
| JP | 2011-508219 A | 3/2011 |
| JP | 2013-137332 A | 7/2013 |
| WO | 98/16814 A1 | 4/1998 |
| WO | 99/47963 A1 | 9/1999 |
| WO | 00/66985 A1 | 11/2000 |
| WO | 02/12864 A1 | 2/2002 |
| WO | 2006/084283 A2 | 8/2006 |
| WO | 2007/010803 A1 | 1/2007 |
| WO | 2007/118209 A2 | 10/2007 |
| WO | 2007/147159 A2 | 12/2007 |
| WO | 2008/007580 A1 | 1/2008 |
| WO | 2008-080417 A1 | 7/2008 |
| WO | 2009/117033 A2 | 9/2009 |
| WO | 2011/108369 A1 | 9/2011 |
| WO | 2012/014778 A1 | 2/2012 |

OTHER PUBLICATIONS

U.S. Office Action dated Apr. 2, 2013, issued in related U.S. Appl. No. 13/596,280 (13 pages).
Kask, Peet et al., "Two-Dimensional Fluorescence Intensity Distribution Analysis: Theory and Applications", Biophysical Journal, Apr. 2000, vol. 78, p. 1703-1713.
Chinese Office Action dated Aug. 13, 2013, issued in related Chinese application No. 201180011655.3; w/ English Translation (16 pages).
International Search Report dated Mar. 29, 2011, issued in related PCT/JP2011/053483.
International Preliminary Report on Patentability (PCT/IPEA/409) issued in related PCT/JP2011/053483.
Chinese Office Action dated Aug. 9, 2013, issued in related Chinese application No. 201180011640.7; w/ English Translation (16 pages).
International Search Report dated Mar. 29, 2011, issued in related PCT/JP2011/053482.
International Preliminary Report on Patentability (PCT/IPEA/409) issued in related PCT/JP2011/053482.
Notice of Allowance dated Mar. 27, 2013, issued in related U.S. Appl. No. 13/597,825 (8 pages).
Chinese Office Action dated Feb. 7, 2013, issued in related Chinese application No. 201180011644.5; w/ English Translation (18 pages).
Extended European Search Report dated Mar. 28, 2013, issued in related EP application No. 11750481.1.
International Search Report dated Mar. 29, 2011, issued in related PCT/JP2011/053481.
International Preliminary Report on Patentability (PCT/IPEA/409) issued in related PCT/JP2011/053481.
Goodwin, Peter et al., "Rapid Sizing of Individual Fluorescently Stained DNA Fragments by Flow Cytometry," Nucleic Acids Research, 1993, vol. 21, No. 4, p. 803-806.
Keller, Richard et al., "Single-Molecule Fluorescence Analysis in Solution," Applied Spectroscopy, 1996, vol. 50, No. 7, p. 12A-32A.
Lee, Yuan-Hsiang et al., "Laser-Induced Fluorescence Detection of a Single Molecule in a Capillary," Analytical Chemistry, dated Dec. 1, 1994, vol. 66, No. 23, p. 4142-4149.
Li, Haitao et al., "Ultrasensitive Coincidence Fluorescence Detection of Single DNA Molecules," Analytical Chemistry, dated Apr. 1, 2003, vol. 75, No. 7, p. 1664-1670.
Nie, Shuming et al., "Probing Individual Molecules with Confocal Fluorescence Microscopy," Science, dated Nov. 11, 1994, vol. 266, p. 1018-1021.
Tahari, Abdel. "Fluorescence Correlation Spectroscopy: Ultrasensitive Detection in Clear and Turbid Media," University of Illinois, 2006, p. 1-88.
Wu, Alan et al., "Development and Preliminary Clinical Validation of a High Sensitivity Assay for Cardiac Troponin Using a Capillary Flow (Single Molecule) Fluorescence Detector," Clinical Chemistry, 2006, vol. 52, No. 11, p. 2157-2159.
Itoh et al., "A New Method for Detection of Influenza Viruses by Single Particle-Recognition Based on the Principle of Fluorescence Correlation Spectroscopy," Chemistry and Biology, 2009, vol. 47, No. 12, p. 823-830; with partial translation.
Carlsson, K. et al., "Three-dimensional Microscopy Using a Confocal Laser Scanning Microscope", Optics Letters, Optical Society of America, Feb. 1985, vol. 10, No. 2, p. 53-55, XP007922413.
U.S. Office Action dated Oct. 4, 2013, issued in related U.S. Appl. No. 13/596,243 (15 pages).

(56) References Cited

OTHER PUBLICATIONS

Japanese Office Action dated Dec. 18, 2012 issued in related JP application No. 2012-503060; w/ English Translation (6 pages).
Sando, Shinsuke et al. "Quencher as Leaving Group: Efficient Detection of DNA-Joining Reactions", Journal of the American Chemical Society, 2002, vol. 124, No. 10, p. 2096-2097.
Kask, Peet et al. "Fluorescence-Intensity Distribution Analysis and its Application in Biomolecular Detection Technology", PNAS, Nov. 23, 1999, vol. 96, No. 24, p. 13756-13761.
International Search Report dated Sep. 20, 2011, issued in related PCT/JP2011/066576.
U.S. Office Action dated Feb. 20, 2014, issued in related U.S. Appl. No. 13/746,968 (11 pages).
Kato, Noriko et al., "A Single Molecule Analyzer that Enables New Analysis of DNA and Protein Interactions", Gene & Medicine, 2002, vol. 6, No. 2, p. 271-277; with partial Translation.
U.S. Office Action dated May 22, 2014, issued in related U.S. Appl. No. 13/746,968 (10 pages).
U.S. Office Action dated Jan. 3, 2013, issued in related U.S. Appl. No. 13/597,825 (5 pages).
Chinese Office Action dated Jul. 14, 2014, issued in related Chinese application No. 201180036710.4; w/ English Translation (12 pages).
Extended European Search Report dated Sep. 24, 2014, issued in corresponding European Application No. 12774419.1. (9 pages).
Kinjo, Masataka, "Single molecule protein, nucleic acid, and enzyme assays and their procedures; Single molecule detection by fluorescence correlation spectroscopy", Proteins, Nucleic Acids and Enzymes, 1999, vol. 44, No. 9, pp. 1431-1438, w/ English translation.
Meyer-Almes, F.J., "Nanoparticle Immunoassays: A new Method for Use in Molecular Diagnostics and High Throughput Pharmaceutical Screening based on Fluorescence Correlation Spectroscopy", edit. R. Rigler, Springer, Berlin, 2000, pp. 204-224.
Katoh, Noriko et al., "A single molecule analyzer that enable new analysis of DNA and protein interaction", Genetic Medicine, 2002, vol. 6, No. 2, pp. 271-277.
International Search Report dated Jul. 24, 2012, issued in corresponding application No. PCT/JP2012/060487.
European Communication Pursuant to Article 94(3) EPC dated Nov. 20, 2014, issued in related European Patent Application No. 11812369.4 (6 pages).
Shuming N. et al., "Real-Time Detection of Single Molecules in Solution by Confocal Fluorescence Microscopy", Analytical Chemistry, American Chemical Society, vol. 67, No. 17, pp. 2849-2857, (1995), Cited in European Communication dated Nov. 20, 2014.
U.S. Office Action dated Apr. 13, 2015, issued in U.S. Appl. No. 13/746,968 (19 pages).
Office Action dated Mar. 25, 2015, issued in Chinese Patent Application No. 201180036710.4, with English translation (8 pages).
Office Action dated May 19, 2015, issued in Japanese Patent Application No. 2012-526460 with English translation (8 pages).
Communication pursuant to Article 94(3) EPC dated May 13, 2015, issued in European Patent Application No. 11812369.4 (5 pages).

\* cited by examiner

QUANTITATIVE DETERMINATION METHOD FOR TARGET PARTICLES, PHOTOMETRIC ANALYSIS DEVICE, AND COMPUTER PROGRAM FOR PHOTOMETRIC ANALYSIS

BACKGROUND OF THE INVENTION

1. Field of the Invention

The present invention relates to a method for determining the concentration of particles dispersed and moving at random in a sample solution, by using an optical system which can detect light from a micro region in a solution such as an optical system of a confocal microscope or a multiphoton microscope.

Priority is claimed on Japanese Patent Application No. 2011-092168, filed Apr. 18, 2011, the content of which is incorporated herein by reference.

The present application is a U.S. continuation application based on the PCT International Patent Application, PCT/JP2012/060487, filed on Apr. 18, 2012, the contents of which are incorporated herein by reference.

2. Description of the Related Art

According to the developments in photometric measurement techniques in recent years, detection/measurement of faint light at a single photon or single fluorescent molecule level have become possible by using an optical system of a confocal microscope and a super high sensitive light detection technique capable of the photon counting (single photon detection). Thus, various devices or methods of performing the detection of intermolecular interaction or binding/dissociating reaction of biological molecules, etc. by using such a faint light measurement technique, have been proposed. For example, in Fluorescence Correlation Spectroscopy (FCS, see e.g. Japanese Unexamined Patent Application, First Publication No. 2005-098876; Japanese Unexamined Patent Application, First Publication No. 2008-292371; Masataka Kinjo; "Protein, Nucleic acid, and Enzyme" Vol. 44, No. 9, pages 1431-1438, 1999.; Meyer-Alms; "Fluorescence Correlation Spectroscopy" edt. R. Rigler, Springer, Berlin, pages 204-224, 2000.; and Noriko Kato, et al. "Gene & Medicine", Vol. 6, No. 2, pages 271-277, 2002.), by using an optical system of a laser confocal microscope and a photon counting technique, the measurement is performed on the fluorescence intensity from fluorescence molecules or fluorescently labeled molecules (fluorescent molecules, etc.), entering and exiting a micro region in a sample solution (the focal region to which the laser light of the microscope is condensed, called a "confocal volume"). Based on the average dwell time (translational diffusion time) of the fluorescent molecules, etc. and the average number of the dwelling molecules in the micro region, determined from the autocorrelation function value of the measured fluorescence intensity, the information, such as the speed of the movement, the size, and the concentration of the fluorescent molecules, etc. are acquired, or various phenomena, such as a change of a molecular structure or size, a binding/dissociating reaction, and dispersion/aggregation of molecules, are detected. Moreover, in Fluorescence Intensity Distribution Analysis (FIDA, e.g. Japanese Patent No. 4023523) or Photon Counting Histogram (PCH, e.g. PCT International Publication No. WO 2008-080417), a histogram is made on the fluorescence intensity of fluorescent molecules, etc., entering and exiting a confocal volume, measured similarly to FCS. The average value of the characteristic brightness of the fluorescent molecules, etc. and the average number of molecules dwelling in the confocal volume are calculated by fitting a statistical model formula to the distribution of the histogram. Based on the information thereof, the change of the molecular structure or size, binding/dissociative conditions, and dispersion/aggregation conditions of molecules are estimated. Furthermore, Japanese Unexamined Patent Application, First Publication No. 2007-20565 and Japanese Unexamined Patent Application, First Publication No. 2008-116440 propose methods of detecting fluorescent substances based on a time progress of a fluorescence signal of a sample solution measured by using an optical system of a confocal microscope. In Japanese Unexamined Patent Application, First Publication No. H04-337446, faint light from fluorescent fine particles flowing through a flow cytometer or fluorescent fine particles fixed on a substrate is measured by using a photon counting technique. Moreover, there is proposed a signal calculation processing technique for detecting the existences of the fluorescent fine particles in the flow or on the substrate from the faint light.

Especially, according to the method employing the fluorescence measurement technique of a micro region by using an optical system of a confocal microscope and a photon counting technique, such as FCS and FIDA, the concentration and the amount of the sample required for the measurement may be extremely small (an amount used in one measurement is about several tens of µL at most), as compared with the prior art, and the measuring time is also shortened a lot (in one measurement, a measuring process taking a time of a second order is repeated several times). Thus, those techniques are expected to be a strong tool enabling an experiment or a test at low cost or quickly in comparison with conventional biochemical methods, especially in conducting an analysis of rare or expensive samples which are often used in the field of medical or biological research and development, or in conducting a test of a large number of specimens, such as clinical diagnosis of diseases or the screening of bioactive substances.

SUMMARY OF THE INVENTION

The inventors of the present invention have discovered the following two points in a case where light emitted from a particle as the object of observation which is dispersed and moving at random in a sample solution (concretely, it is a luminescent probe bound to a target particle, or a luminescent probe. The same will apply in the following description) is detected as an indicator by a method for quantifying target particles which are dispersed and moving at random in a sample solution. This has led to the completion of the present invention. That is, the points are that: (1) even if the concentration of the target particles in the sample solution is extremely low, the target particles can be detected highly sensitively by detecting the particles serving as the object of observation with use of the scanning molecular counting method; and (2) it is possible, by using a calibration curve formed from the measurement results of standard sample solutions having known concentrations of the particles as the object of observation, to calculate the concentration of the target particles in the sample solution from the number of the particles as the object of observation obtained by the scanning molecular counting method.

Here, the scanning molecular counting method is a novel photometric analysis technique proposed by the applicant of this application in Japanese Patent Application No. 2010-044714.

That is, the quantitative determination method for target particles according to the first aspect of the present invention is a method for quantifying target particles which are dispersed and moving at random in a sample solution, comprising: (a) preparing a sample solution containing the target particles and luminescent probes to be bound to the target particles, and binding the target particles and the luminescent probes in the sample solution; (b) moving a position of a light detection region of the optical system in the sample solution, with use of an optical system of a confocal microscope or a multiphoton microscope, and detecting light signals emitted from the luminescent probe in the light detection region, and individually detecting the target particle directly or indirectly, while moving the position of the light detection region of the optical system in the sample solution; and (c) counting the number of the target particles detected in the detecting, and calculating the concentration of the target particles in the sample solution from the number of the counted target particles, on the basis of a calibration curve that approximates the correlation between the concentration or quantity of the target particles in the sample solution and the number of the target particles.

According to a second aspect of the present invention, moving the position of the light detection region may be done at a predetermined speed, in the first aspect.

According to a third aspect of the present invention, moving the position of the light detection region may be done at a speed higher than the speed of diffusional movement of either quicker ones of the luminescent probes or the target particles bound to the luminescent probes, in either one aspect of the first aspect and the second aspect.

According to a fourth aspect of the present invention, detecting that the luminescent probe or the target particle bound to the luminescent probe has entered the light detection region may be done, based on the shape of the chronological detected light signal, in the detecting, in any one aspect from the first aspect to the third aspect.

According to a fifth aspect of the present invention, it may be that: the luminescent probe has an energy donor site and an energy acceptor site, which produce a fluorescence energy transfer phenomenon when these sites are close to each other; the distance between the energy donor site and the energy acceptor site is different between a binding state where the luminescent probe is bound to the target particle and a non-binding state where the luminescent probe is not bound to the target particle; and an emission characteristic of light emitted from the luminescent probe is different between the binding state and the non-binding state, in any one aspect from the first aspect to the fourth aspect.

According to a sixth aspect of the present invention, it may be that: the target particle is a nucleic acid; and the luminescent probe is a single stranded nucleic acid which is specifically hybridizable with the target particle, and which is bound with at least either one of a fluorescent substance serving as an energy donor and a substance serving as an energy acceptor in a fluorescence energy transfer phenomenon, in any one aspect from the first aspect to the fifth aspect.

According to a seventh aspect of the present invention, it may be that the method further comprises (d) separating a luminescent probe which is not bound to the target particle from the sample solution, and collecting a complex including the target particle and the luminescent probe, after the (a), in any one aspect from the first aspect to the sixth aspect.

According to an eighth aspect of the present invention, it may be that the method further comprises (e) dissociating the luminescent probe from the complex having been collected in the (d), thereafter separating the free luminescent probe and the target particle from each other, and collecting them, in the seventh aspect.

A photometric analysis device according to a ninth aspect of the present invention is a photometric analysis device for detecting light from a plurality of luminescent particles dispersed and moving at random in a sample solution, with use of an optical system of a confocal microscope or a multiphoton microscope, wherein the device comprising: a light detection region mover for moving a position of a light detection region of the optical system in the sample solution by changing an optical path of the optical system; a light detector for detecting light from the luminescent particle in the light detection region; a signal processor for, while moving the position of the light detection region in the sample solution, individually detecting light signals of the light emitted from respective ones of the luminescent particles detected in the light detector, and counting the number of the luminescent particles detected during the moving of the position of the light detection region by counting the number of the individually detected light signals from the luminescent particles; a storage for storing a calibration curve that approximates the correlation between the concentration or quantity of the luminescent particles in the sample solution and the number of the luminescent particles counted from the sample solution; a concentration calculator for, on the basis of the calibration curve, calculating the concentration of the luminescent particles in the sample solution from the number of the luminescent particles counted in the signal processor; and a display for displaying the concentration of the luminescent particles in the sample solution calculated by the concentration calculator.

According to a tenth aspect of the present invention, it may be that the light detection region mover moves the position of the light detection region at a predetermined speed, in the ninth aspect.

According to an eleventh aspect of the present invention, it may be that the light detection region mover moves the position of the light detection region at a speed higher than the speed of diffusional movement of the luminescent particle, in either one aspect of the ninth aspect and the tenth aspect.

According to a twelfth aspect of the present invention, it may be that the signal processor detects that one of the luminescent particles has entered the light detection region, based on the shape of the chronological detected light signals in the light detector, in any one aspect from the ninth aspect to the eleventh aspect.

According to a thirteenth aspect of the present invention, it may be that the signal processor detects that one of the luminescent particles has entered the light detection region, when the light signal having an intensity greater than a predetermined threshold value is detected, in the twelfth aspect.

According to a fourteenth aspect of the present invention, it may be that the signal processor determines the number density or concentration of the luminescent particles in the sample solution, on the basis of the number of the detected luminescent particles, in any one aspect from the ninth aspect to the thirteenth aspect.

According to a fifteenth aspect of the present invention, it may be that the luminescent particle is a target particle bound to a luminescent probe; and light detected in the light detector is light emitted from the luminescent probe in a binding state to the target particle, in any one aspect from the ninth aspect to the fourteenth aspect.

According to a sixteenth aspect of the present invention, it may be that light detected in the light detector is light emitted from the luminescent probe having been freed from a complex including the target particle and the luminescent probe, in any one aspect from the ninth aspect to the fourteenth aspect.

A computer readable storage device according to a seventeenth aspect is a computer readable storage device, having a computer program product including programmed instructions for photometric analysis of detecting light from a luminescent particle dispersed and moving at random in a sample solution, with use of an optical system of a confocal microscope or a multiphoton microscope, the programmed instructions causing a computer perform steps of: changing the optical path of the optical system, so as to move a position of a light detection region of the optical system in the sample solution; detecting the light from the luminescent particle in the light detection region, while moving the position of the light detection region in the sample solution; individually detecting a light signal of the light emitted from respective ones of the detected luminescent particle; counting the number of the luminescent particles detected during the moving of the position of the light detection region by counting the number of the individually detected light signals of the light from the luminescent particles; and calculating the concentration of the target particles in the sample solution from the counted number of the plurality of the luminescent particles on the basis of a calibration curve that approximates the correlation between the concentration quantity of the luminescent particles in the sample solution and the number of the luminescent particles counted from the sample solution.

According to an eighteenth aspect of the present invention, it may be that the position of the light detection region is moved at a predetermined speed, in the changing step, in the seventeenth aspect.

According to a nineteenth aspect of the present invention, it may be that the position of the light detection region is moved at a speed higher than the speed of diffusional movement of the luminescent particle, in the changing procedure, in either one aspect of the seventeenth aspect and the eighteenth aspect.

According to a twentieth aspect of the present invention, detecting that one of the luminescent particles has entered the light detection region, may be done based on the shape of the chronological detected light signal, in the light signal detection procedure, in any one aspect from the seventeenth aspect to the nineteenth aspect.

According to a twenty first aspect of the present invention, detecting that one of the luminescent particles has entered the light detection region, may be done when a light signal having an intensity greater than a predetermined threshold value is detected, in the light signal detection procedure, in any one aspect from the seventeenth aspect to the twentieth aspect.

According to a twenty second aspect of the present invention, it may be that the program further comprises a procedure for determining the number density or concentration of the luminescent particles in the sample solution, on the basis of the number of the detected luminescent particles, in any one aspect from the seventeenth aspect to the twenty first aspect.

According to a twenty third aspect of the present invention, it may be that light detected from the light detection region is light emitted from the luminescent probe in a binding state to the target particle, in the light detection procedure, in any one aspect from the seventeenth aspect to the twenty second aspect.

According to a twenty fourth aspect of the present invention, it may be that light detected from the light detection region is light emitted from the luminescent probe having been freed from a complex including the target particle and the luminescent probe, in the light detection procedure, in any one aspect from the seventeenth aspect to the twenty second aspect.

DETAILED DESCRIPTION OF THE PREFERRED EMBODIMENTS

Figure 1A:
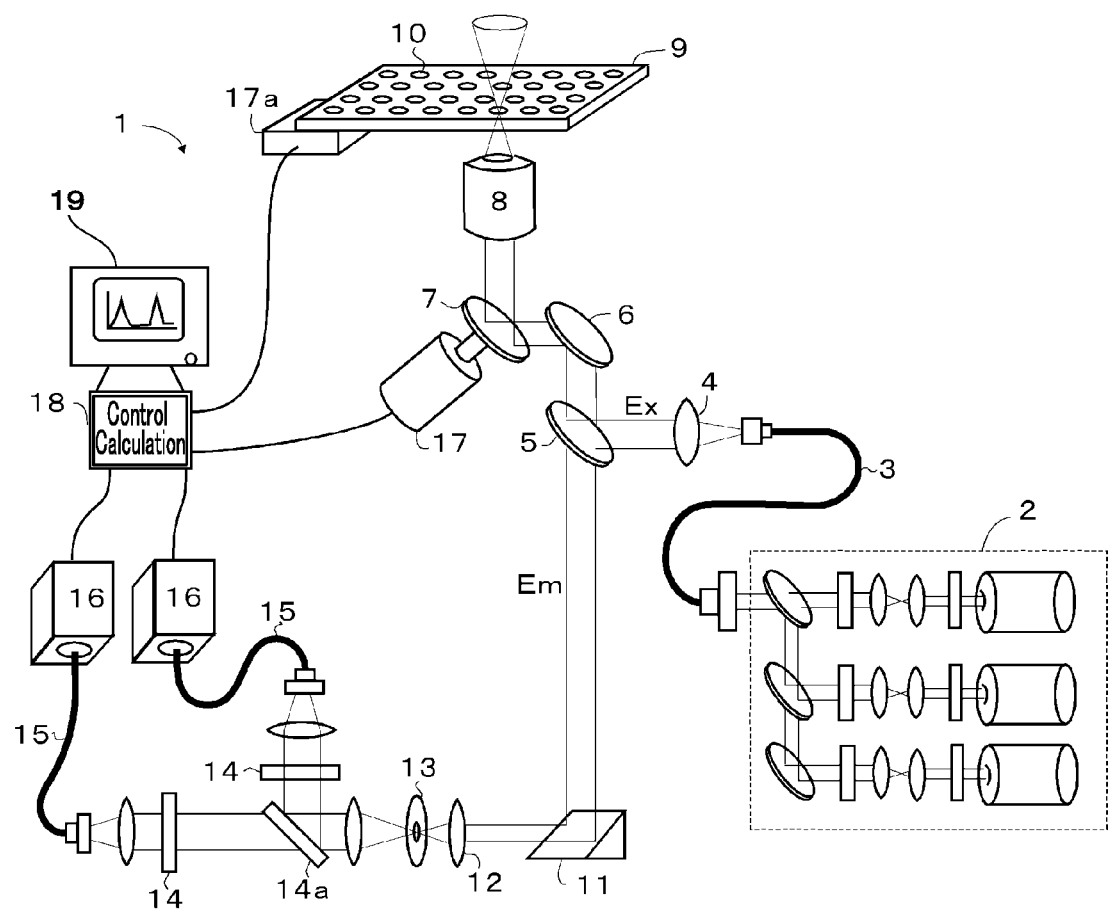
FIG. 1A is a schematic diagram of the internal structure of a photometric analysis device for the scanning molecular counting method.

Firstly, the scanning molecular counting method according to one embodiment of the present invention is described. In the scanning molecular counting method, while scanning the inside of a sample solution with a micro region, light emitted from a luminescent particle dispersed and moving at random in the sample solution (hereunder, referred to as "luminescent particle") in the micro region, is detected when the luminescent particle passes across the inside of the micro region. Thus, the scanning molecular counting method makes possible, by individually detecting a plurality of luminescent particles in the sample solution one by one, the counting of the luminescent particles, and the acquisition of the information about the concentration or number density of the luminescent particles in the sample solution. Similarly to the photometric analysis techniques such as FIDA, the amount of the sample required for the measurement may be extremely small (e.g., several tens of µL). Moreover, the measuring time is short, and furthermore, it becomes possible to quantitatively detect the characteristics of the luminescent particles, such as its concentration or number density, even when the concentration or number density thereof are lower than the cases of the photometric analysis techniques such as FIDA.

The luminescent particle means a particle which emits light by fluorescence, phosphorescence, chemiluminescence, bioluminescence, light scattering, etc. In the quantitative determination method for target particles according to one embodiment of the present invention, the luminescent particle is made by binding of a target particle and a luminescent probe.

In one embodiment of the present invention, the term "light detection region" of an optical system of a confocal microscope or a multiphoton microscope, is a micro region where light is detected in these microscopes, and corresponds to the region to which illumination light is condensed when the illumination light is given from an object lens. This light detection region is determined in accordance with the spatial relationship of an object lens and a pinhole especially in a confocal microscope.

The detection of light is sequentially performed while moving the position of the light detection region in the sample solution, that is, while scanning the inside of the sample solution with the light detection region. When the light detection is performed and when the moving light detection region includes a luminescent probe bound to or associated with a randomly moving particle, light from the luminescent probe is detected. By so doing, the existence of one particle is detected. At this time, the existence of the particle desired to be detected (target particle) may be directly detected or indirectly detected. The case of direct detection is performed by detecting a luminescent probe bound to the target particle. The case of indirect detection is performed by detecting light from a luminescent probe dissociated from the target particle after once being bound to the particle. In these cases, the light signal from each luminescent probe is individually detected with sequentially detected light, by which the existence of a particle is individually and sequentially detected one by one, and thereby various information on the condition of the particle within the solution are acquired. Concretely, for example, in the above-mentioned structure, the number of the particles detected during the moving of the position of the light detection region may be counted by counting the number of the individually detected particles (the counting of particles). According to this structure, by combining the number of the particles and the moving amount of the position of the light detection region, the information on the number density or concentration of the particles in the sample solution can be acquired. Especially, if the whole volume of the moving track of the position of the light detection region is determined by an arbitrary method, for example, by moving the position of the light detection region at a predetermined speed, the number density or concentration of the particles can be concretely computed. Of course, instead of determining directly the absolute number density value or concentration value, the relative ratio of the number density or concentration, to a plurality of sample solutions or a standard sample solution that becomes a reference of a concentration or a number density, may be computed. Moreover, since the scanning molecular counting method is designed to move the position of the light detection region by changing the optical path of the optical system, the light detection region moves quickly and substantially no mechanical vibration nor hydrodynamic action will be generated in the sample solution. By so doing, the light can be measured under a stable condition where the particles as the object of detection are not influenced by such a mechanical action. At this time, when a vibration or flow is applied to the inside of the sample solution, the physical characteristics of the particles may be changed. Moreover, since there is no need of a structure to make the sample solution circulate, the measurement and the analysis are possible with an extremely small amount (about one to several tens of µL) of the sample solution similarly to FCS, FIDA, and the like.

In the above-mentioned individually detecting the particle, the judgment from the chronological detected light signals regarding whether or not a luminescent probe has entered the light detection region may be done based upon the shape of a chronological detected light signal. This luminescent probe includes a case where one luminescent probe is bound to one particle, a case where a plurality of luminescent probes are bound to one particle, and a case where luminescent probe(s) is/are dissociated from one particle after being bound to the particle, depending on the embodiment. The same will apply in the following description.

In the embodiments, typically, the structure may be designed to detect that a luminescent probe has entered the light detection region when a light signal having an intensity greater than a predetermined threshold value is detected. Here, the predetermined threshold value means a preset value of light intensity, and a value having been set experimentally or in order to meet the purpose of the analysis.

Moreover, in the above-mentioned step of moving the position of the light detection region, the speed of moving the position of the light detection region in the sample solution may be appropriately modified based on the characteristic of the luminescent probe, or the number density or concentration in the sample solution. As understood by ones ordinarily skilled in the art, the manner of light detected from the luminescent probe may be different depending on the characteristic, or the number density or concentration in a sample solution. Especially, when the speed of moving the light detection region is higher, the amount of light obtained from the luminescent probe will be reduced. Therefore, it is preferable to appropriately modify the speed of moving the light detection region so that the light from the luminescent probe can be measured with good precision or good sensitivity.

Furthermore, in moving the position of the light detection region, the speed of moving the position of the light detection region in the sample solution may be set to be higher than the speed of diffusional movement of the luminescent probes bound to the target particles serving as the object of detection (the average moving speed of particles owing to the Brownian motion). As explained above, in the scanning molecular counting method, light emitted from a luminescent probe is detected when the light detection region passes through the position where the luminescent probe bound to one particle exists, thereby detecting the luminescent probe individually. However, if the luminescent probe bound to the particle moves at random owing to the Brownian motion in the solution to thereby enter and exit the light detection region multiple times, the light signal showing the existence of the particle desired to be detected will be detected from one luminescent probe multiple times. As a result, it becomes difficult to establish a correspondence between the detected light signal and the existence of one particle desired to be detected. Therefore, as described above, the speed of moving the light detection region is set higher than the speed of diffusional movement of the luminescent probes bound to the particles. Concretely, the speed of moving the light detection region is set higher than the speed of diffusional movement of the luminescent probes in a binding state to the target particles. Moreover, in the case where the target particle is indirectly detected by detecting a light signal emitted from the luminescent probe (in other words, the case where the particle as the object of observation is a luminescent probe), the speed of moving the light detection region is set so that it can move at a speed higher than the speed of diffusional movement of the luminescent probes. That is, the position of the light detection region is set so that it can move at a speed higher than the speed of diffusional movement of either quicker ones of the luminescent probes or the target particles bound to the luminescent probes. By so doing, it becomes possible to establish a correspondence between a luminescent probe and one light signal (showing the existence of one particle). Since the speed of diffusional movement is different depending upon the particles as the object of observation, it is preferable to appropriately modify the speed of moving the light detection region according to the characteristics (especially, the diffusion constant) of the particle as the object of observation.

The optical path of the optical system for moving the position of the light detection region may be changed in an arbitrary way.

For example, the optical path may be changed by using a galvanomirror employed in the laser scan type light microscope so that the position of the light detection region can be changed. The movement track of the position of the light detection region may be set arbitrarily, for example, which may be selectable from circular, elliptical, rectangular, straight, and curvilinear ones.

The scanning molecular counting method is designed so that its light detecting mechanism itself has a structure to detect light from a light detection region in a confocal microscope or a multiphoton microscope similarly to the cases of photometric analysis techniques such as FIDA. Thus, the amount of a sample solution may be extremely small in the same way. However, since no statistical process such as computing the fluorescence intensity fluctuation is executed in the scanning molecular counting method, the photometric analysis technique of the scanning molecular counting method is applicable to a sample solution in which the number density or concentration of particles is much lower than the level required for the photometric analysis techniques such as FIDA.

Moreover, in the scanning molecular counting method, each of the particles dispersed or dissolved in a solution is individually detected. Thus, it is possible, by using the information, to quantitatively count the particles, calculate the concentration or number density of the particles in the sample solution, or acquire the information about the concentration or number density. That is, according to the scanning molecular counting method, the particles are detected one by one by establishing a one-on-one correspondence between a particle passing through the light detection region and a detected light signal. By so doing, the counting of particles dispersed and moving at random in a solution becomes possible, and also it becomes possible to determine the concentration or number density of particles in a sample solution more precisely as compared with the conventional art. According to the above-mentioned quantitative determination method for target particles to determine the particle concentration by individually detecting luminescent probes and counting the number thereof, the quantitative measurement of the target particles is possible even if the concentration of the luminescent probes in the sample solution is much lower than the concentration which can be determined based upon the fluorescence intensity measured by a fluoresce spectrometer or a plate reader.

Furthermore, according to the manner of scanning the inside of a sample solution with a light detection region by changing the optical path of an optical system, the inside of the sample solution is observed uniformly or under a condition where the sample solution is mechanically stable without applying a mechanical vibration nor a hydrodynamic action to the sample solution. Generally, when a flow is given to the sample, it is difficult to give an always uniform flow speed and the device structure becomes complicated. Moreover, the required amount of the sample largely increases, and the particle, the luminescent probe, the combined body thereof, or another substance, in the solution may be deteriorated or denaturalized by the hydrodynamic action owing to the flow. According to this embodiment, the observation is carried out without applying a mechanical vibration or a hydrodynamic action to the sample solution, and thus, the reliability of the quantitative detection result is improved as compared with e.g., the case in which a flow is generated in a sample. Moreover, the measurement can be carried out under a condition where there are no influences or artifacts due to dynamic action against the particles serving as the object of detection in the sample solution.

<The Structure of a Photometric Analysis Device for the Scanning Molecular Counting Method>

Figure 1B:
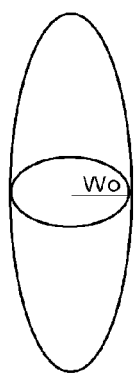
FIG. 1B is a schematic diagram of a confocal volume (an observation region of a confocal microscope).

In the basic structure, the scanning molecular counting method can be realized with a photometric analysis device formed by combining an optical system of a confocal microscope and a photodetector as schematically illustrated in FIG. 1A, with which FCS, FIDA, etc. can be performed. Referring to FIG. 1A, the photometric analysis device 1 consists of an optical system 2-17 and a computer 18 for acquiring and analyzing data as well as controlling the operation of each part in the optical system. The optical system of the photometric analysis device 1 may be the same as the optical system of a usual confocal microscope. Laser light emitted from a light source 2 and transmitted through the inside of a single mode fiber 3 (Ex) forms light diverging to be radiated at an angle decided by an inherent NA at the emitting end of the fiber. The radiated light forms a parallel beam with a collimator 4, is reflected on a dichroic mirror 5 and reflective mirrors 6 and 7, and enters an object lens 8. Typically, above the object lens 8 is placed a sample container or a micro plate 9 having wells 10 arranged therein, to which one to several tens of μL of a sample solution is dispensed. The laser light emitted from the object lens 8 is focused in the sample solution in the sample container or well 10, forming a region having a strong light intensity (excitation region). In the sample solution, particles serving as the object of observation and luminescent probes to be bound to these particles, typically, molecules to which a light emitting label such as a fluorescent dye is attached, are dispersed or dissolved. When a particle which has been bound to or associated with a luminescent probe (it may be a luminescent probe dissociated from a particle after once being bound to the particle, depending on the embodiment) enters the excitation region, the luminescent probe is excited and emits light during the period. The emitted light (Em) passes through the object lens 8 and the dichroic mirror 5, is reflected on the mirror 11, and condensed by a condenser lens 12. The condensed light passes through the pinhole 13, transmits through a barrier filter 14 (where light components only in a specific wavelength band region are selected), and is introduced into a multimode fiber 15, reaching to a photodetector (light detector) 16. Then, after the conversion into chronological electric signals in the photodetector 16, the signals are inputted into the computer 18, where the processes for optical analyses are executed in manners explained later. As known to ones skilled in the art, in the above-mentioned structure, the pinhole 13 is located at a conjugate position of the focal position of the object lens 8. Thereby, as schematically shown in FIG. 1B, only the light emitted from the focal region of the laser light, i.e., the excitation region, passes through the pinhole 13 while the light from regions other than the excitation region is blocked. The focal region of the laser light illustrated in FIG. 1B is a light detection region in this photometric analysis device, whose effective volume is usually about 1-10 fL (Typically, the light intensity is spread in accordance with a Gaussian type or Lorentz type distribution having the peak at the center of the region. The effective volume is a volume of an approximate ellipsoid bordering a surface where the light intensity is reduced to $1/e^2$ of the peak intensity.), which is called as "confocal volume". Moreover, light from one combined body of the particle and the luminescent probe, or the luminescent probe, for example faint light from one or several fluorescent dye molecule(s), is detected in the scanning molecular counting method. For this reason, a super high sensitive photodetector, usable for the photon counting, may be used for the photodetector 16. Moreover, on the stage (not shown) of the microscope may be provided a stage position changing apparatus 17a for moving the horizontal position of the micro plate 9, in order to change the well 10 to be observed. The operation of the stage position changing apparatus 17a may be controlled by the computer 18. According to this structure, quick measurement can be achieved even if a plurality of specimens are present.

Figure 1C:
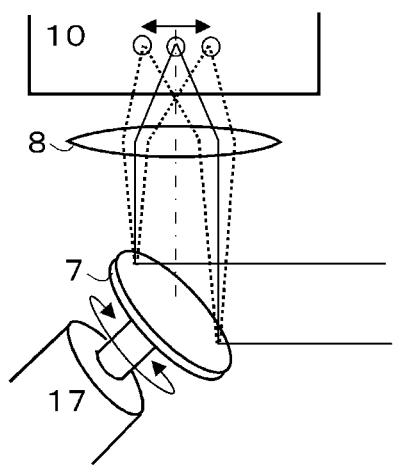
FIG. 1C is a schematic diagram of a mechanism for changing the direction of a reflective mirror to move the position of a light detection region in a sample solution.

Furthermore, in the optical system of the above-mentioned photometric analysis device is provided a mechanism for changing the optical path of the optical system to scan the inside of the sample solution with the light detection region, in other words, for moving the position of the focal region (i.e., the light detection region), within the sample solution. For this mechanism for moving the position of the light detection region, for example, as schematically illustrated in FIG. 1C, a mirror deflector 17 for changing the direction of the reflective mirror 7 may be employed. This mirror deflector 17 may be the same as that of a galvanomirror device equipped on a usual laser scan type microscope. Moreover, in order to attain a desired moving pattern of the position of the light detection region, the mirror deflector 17 is driven in harmony with the light detection of the photodetector 16 under the control of the computer 18. The movement track of the position of the light detection region may be arbitrarily selected from circular, elliptical, rectangular, straight, and curvilinear ones, or a combination of these. In other words, the program in the computer 18 may be designed so that various moving patterns can be selected. Although not illustrated, the position of the light detection region may be moved in the vertical direction by moving the object lens 8 up and down. As noted, according to the structure of changing the optical path of the optical system to move the position of the light detection region instead of moving the sample solution, substantially no mechanical vibration or hydrodynamic action will be generated in the sample solution. Consequently it becomes possible to eliminate the influence of a dynamic action on the object of observation, achieving a stable measurement.

In the case that a combined body of a particle and a luminescent probe, or a luminescent probe, emits light by multiple photon absorption, the above-mentioned optical system is used as a multiphoton microscope. In that case, since the light is emitted only from the focal region of the excitation light (light detection region), the pinhole 13 may be removed. Moreover, in the case that a combined body of a particle and a luminescent probe, or a luminescent probe, emits light owing to a chemiluminescence or bioluminescence phenomenon without excitation light, the optical system 2-5 for generating excitation light may be omitted. In a case that a combined body of a particle and a luminescent probe, or a luminescent probe, emits light owing to phosphorescence or scattered light, the above-mentioned optical system of the confocal microscope is used as it is. Furthermore, in the photometric analysis device 1, as shown in the drawing, a plurality of excitation light sources 2 may be provided so that the wavelength of the excitation light can be selected appropriately in accordance with the excitation wavelength of a combined body of a particle and a luminescent probe or a luminescent probe. Similarly, a plurality of photodetectors 16 may also be provided so that, in a case that the sample contains a plurality of kinds of combined bodies of particles and luminescent probes, or luminescent probes, whose wavelengths differ from each other, the respective lights from them can be detected separately in accordance with the wavelengths.

<The Principle of the Photometric Analysis Technique of the Scanning Molecular Counting Method>

Spectral analysis techniques, such as FIDA, are advantageous from the point that the required amount of the sample is extremely small and a test can be executed promptly as compared with the conventional biochemical analytical techniques. However, in the spectral analysis techniques such as FIDA, the concentration and characteristics of the particles as the object of observation are principally calculated based on the fluorescence intensity fluctuation. Therefore, in order to obtain highly precise measurement results, the concentration or number density of the particles as the object of observation in a sample solution should be at a level where about one particle as the object of observation always exists in the light detection region CV during the fluorescence intensity measurement so that a significant light intensity (photon count) can be always detected in the period of the measurement. If the concentration or number density of the particles as the object of observation is lower than that, for example, at the level where the particle as the object of observation rarely enters the light detection region CV, a significant light intensity (photon count) would appear only in a part of the period of the measurement, and thus, highly precise calculation of the light intensity fluctuation would become difficult. Moreover, if the concentration of the particles as the object of observation is much lower than the level where about one particle as the object of observation always exists inside the light detection region during the measurement, the calculation of the light intensity fluctuation would be easily influenced by the background. Furthermore, the period of the measurement should be long in order to obtain a significant quantity of the light intensity data, which is sufficient for the calculation. On the other hand, in the scanning molecular counting method, it is possible to detect the characteristics of the particles as the object of observation, such as its number density or concentration, even if the concentration of the particles as the object of observation is lower than the level required in the spectral analysis techniques such as FIDA.

Figure 2A:
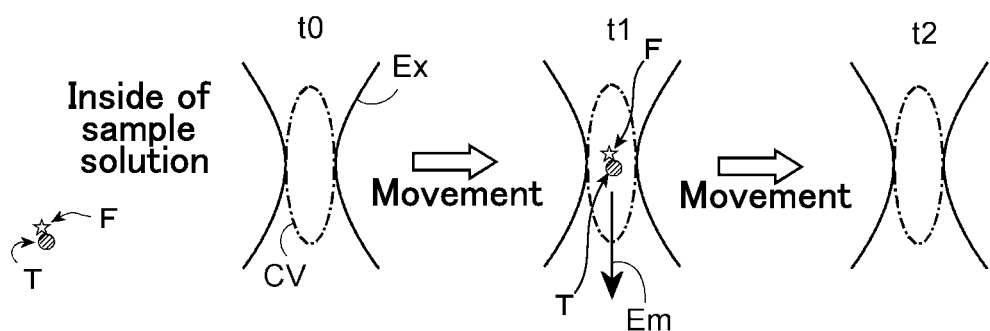
FIG. 2A is a schematic diagram explaining the principle of light detection by the photometric analysis technique for the scanning molecular counting method.
Figure 2B:
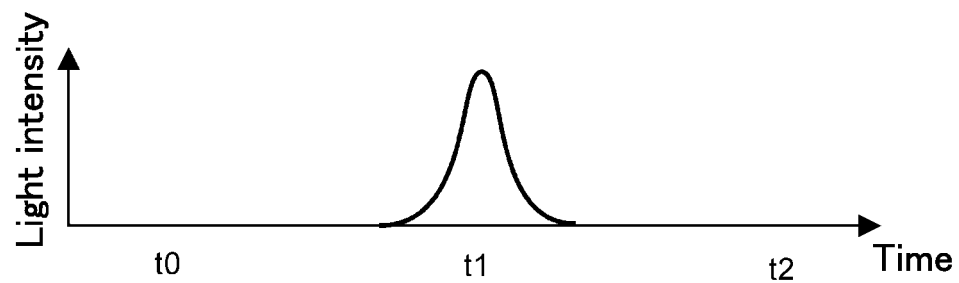
FIG. 2B is a schematic diagram of the chronological change of the measured light intensity.

In the photometric analysis technique of the scanning molecular counting method, briefly speaking, as a process to be executed, light detection is performed while moving the position of the light detection region CV in a sample solution, that is, while scanning the inside of the sample solution with the light detection region CV, by driving the mechanism for moving the position of the light detection region (the light detection region mover: mirror deflector 17) to change the optical path as schematically drawn in FIG. 2A. For example, as shown in FIG. 2A, during the moving of the light detection region CV (in the drawing, time t0-t2), when the light detection region CV passes through a region where one particle (in the drawing, a fluorescent dye F as a luminescent probe bound to a particle T as the object) exists (t1), a significant light intensity (Em) is detected as drawn in FIG. 2B. By executing the moving of the position of the light detection region CV and the light detection as described above and detecting one by one each significant light intensity appearing as illustrated in FIG. 2B during the period, the luminescent probe or the target particle bound to the luminescent probe is detected individually. This embodiment describes the case of direct detection, i.e. the case of detecting a luminescent probe bound to a target particle; however, the case of indirect detection, i.e. the case of detecting light from a luminescent probe dissociated from a target particle after once being bound to the particle, is also possible.

By counting the number of the detected particles, the information about the number, concentration, or number density of the particles existing in the measured region can be acquired. In the principle of this photometric analysis technique of the scanning molecular counting method, no statistical calculation process, such as the calculation of the fluorescence intensity fluctuation, is conducted and the particles are detected one by one. Therefore, it becomes possible to acquire the information about the concentration or number density of particles even with a sample solution whose concentration of the particles to be observed is too low to perform a sufficiently precise analysis in FIDA or the like.

Moreover, according to the method of individually detecting particles in a sample solution and counting them, like the scanning molecular counting method, it is possible to measure a lower concentration than the case of measuring the concentration of fluorescently labeled particles from the fluorescence intensity measured with a fluorescence spectrophotometer or a plate reader. In the case of measuring the concentration of certain fluorescently labeled particles with a fluorescence spectrophotometer or a plate reader, usually, it is assumed that the fluorescence intensity is proportional to the concentration of the fluorescently labeled particles. However, in that case, when the concentration of the fluorescently labeled particles is significantly low, the amount of noise signals becomes large relative to the amount of signals of the light emitted from the fluorescently labeled particles (deterioration of the S/N ratio). As a result, the proportionality relation between the concentration and the amount of light signals of the fluorescently labeled particles collapses, and the precision of the determined concentration value deteriorates. On the other hand, in the scanning molecular counting method, noise signals are eliminated from the detected result in the step of detecting the signals corresponding to the respective particles from the detected light signals, and the concentration is calculated by counting only the signals corresponding to the respective particles. Therefore, it is possible to detect a lower concentration than the case of detecting the concentration under the assumption that the fluorescence intensity is proportional to the concentration of the fluorescently labeled particles.

<Measurement of the Light Intensity of a Sample Solution by the Scanning Molecular Counting Method>

The measurement of the light intensity in the photometric analysis of the scanning molecular counting method may be executed in the same manner as that of the measurement process of the light intensity in FCS or FIDA, except for driving the mirror deflector 17 to move the position of the light detection region within the sample solution (scanning inside of the sample solution) during the measurement. In the operation process, typically, after dispensing a sample solution into the well(s) 10 of the micro plate 9 and placing it on the stage of the microscope, a user inputs a command of starting a measurement into the computer 18. The computer 18 illuminates the light detection region in the sample solution with the excitation light and starts to measure the light intensity, according to the programs stored in a storage device (not shown). These programs include a procedure for changing the optical path in order to move the position of the light detection region in the sample solution (changing procedure), and a procedure for detecting light from the light detection region during the moving of the position of the light detection region (light detection procedure). During this measurement, under the control of the operation process of the computer 18 according to the programs, the mirror deflector 17 drives the mirror 7 (galvanomirror) to move the position of the light detection region in the well 10. Simultaneously with this, the photodetector 16 chronologically converts the detected light into an electric signal and transmits it to the computer 18. The computer 18 generates the chronological light intensity data from the transmitted light signals and stores it in an arbitrary manner. The photodetector 16 is typically a super high sensitive photodetector which can detect an arrival of a single photon, and thus the detection of light is the photon counting executed in the manner of measuring successively the number of photons which arrive at the photodetector for every predetermined unit time (BINTIME), for example, every 10 micro seconds, during a predetermined period of time. The chronological light intensity data may be chronological photon count data.

The speed of moving the position of the light detection region during the measurement of the light intensity may be a predetermined speed which is arbitrarily set, for example, experimentally or in order to meet the purpose of the analysis. In a case of acquiring the information on the number density or concentration based on the number of detected particles as the object of observation, the size or volume of the region through which the light detection region has passed is required. Therefore, the moving of the position of the light detection region is executed in a manner enabling the grasping of the moving distance. Because the interpretation of the measurement result will be easy if the elapsed time during the measurement is proportional to the moving distance of the position of the light detection region, basically, it is preferable that the moving speed is constant, although the speed is not to be limited thereto.

Figure 3A:
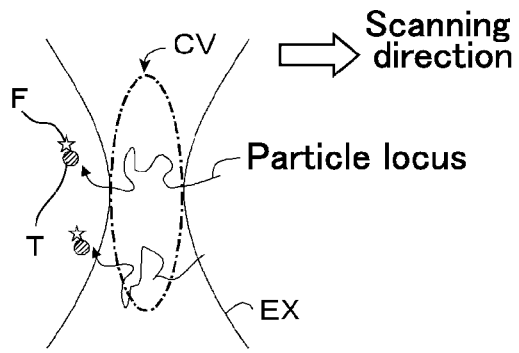
FIG. 3A is a drawing of a model in the case that particles as the object of observation are passing across a light detection region owing to Brownian motion.
Figure 3B:
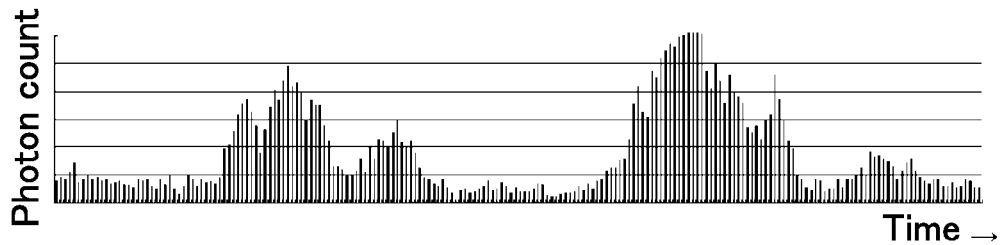
FIG. 3B is a diagram showing an example of the chronological change of the photon counts (light intensity) in FIG. 3A.

By the way, regarding the speed of moving the position of the light detection region, in order to quantitatively and precisely execute the individual detection of the particles as the object of observation from the chronological measured light intensity data or the counting of the number of the particles as the object of observation, it is preferable to set the moving speed to a value higher than the moving speed in the random motion, i.e., Brownian motion of the particle as the object of observation. More strictly, the particle as the object of observation is a combined body of a particle and a luminescent probe, or a luminescent probe having been freed from a particle by decomposition after being bound thereto. In one embodiment of the present invention, it is a target particle bound to a luminescent probe. Since the particle as the object of observation in the photometric analysis technique of the scanning molecular counting method is a particle dispersed or dissolved in a solution and moving at random freely, its position moves with time owing to the Brownian motion. Thus, when the speed of moving the position of the light detection region is slower than the movement of a particle owing to the Brownian motion, the particle moves at random in the region as schematically drawn in FIG. 3A. By so doing, the light intensity changes at random as shown in FIG. 3B, which makes it difficult to specify a significant light intensity change corresponding to each particle as the object of observation. Concretely, as already noted, the excitation light intensity in the light detection region is reduced from the peak at the center of the region toward its outside. Then, as drawn in FIG. 4A, a particle (a fluorescent dye F and a particle T as the object) passes across the light detection region in an approximately straight line. Thereby, the profile of the change of the light intensity corresponding to each particle becomes almost uniform in the chronological light intensity data as illustrated in FIG. 4B. Moreover, the speed of moving the position of the light detection region is set to be higher than the average moving speed of the particles owing to the Brownian motion (speed of diffusional movement) so that the correspondence between each particle T as the object of observation and the light intensity can be easily specified. Here, when a particle passes through the light detection region in an approximately straight line, the profile of the change of the light intensity is similar to the excitation light intensity distribution.

Concretely, the time $\Delta t$ required for a particle as the object of observation (more strictly, a combined body of a particle and a luminescent probe, or a luminescent probe having been freed from a particle by decomposition after being bound thereto) having a diffusion coefficient D to pass through the light detection region of radius Wo (confocal volume) by the Brownian motion is given from the expression of the relation of mean-square displacement:

$$(2Wo)^2 = 6D \cdot \Delta t \qquad (1)$$

as:

$$\Delta t = (2Wo)^2/6D \qquad (2)$$

and thus, the speed of the particle as the object of observation moving by the Brownian motion (speed of diffusional movement) Vdif, becomes approximately $$V\text{dif} = 2Wo/\Delta t = 3D/Wo \qquad (3)$$

Then, with reference to the speed of diffusional movement Vdif, the speed of moving the position of the light detection region may be set to a sufficiently higher value than Vdif. For example, when the diffusion coefficient of the particle as the object of observation is expected to be about $D=2.0\times10^{-10}$ m$^2$/s, Vdif will be $1.0\times10^{-3}$ m/s, supposing Wo is about 0.62 μm, and therefore, the speed of moving the position of the light detection region may be set to about 10 times thereof at 15 mm/s. When the diffusion coefficient of the particle as the object of observation is unknown, an appropriate speed of moving the position of the light detection region may be determined by repeating preliminary experiments with setting various moving speeds of the position of the light detection region in order to find the condition that the profile of the change of the light intensity becomes an expected profile (typically, similar to the excitation light intensity distribution).

<Analysis of Light Intensity by the Scanning Molecular Counting Method>

When the chronological light intensity data of a sample solution are obtained by the above-mentioned processes, an analysis of the light intensity as described below may be executed in the computer 18 through the processes in accordance with the programs stored in a storage device (procedure for detecting light signals individually from respective luminescent particles emitted from detected light (light signal detection procedure)).

(i) Detection of One Particle as the Object of Observation

Figure 4A:
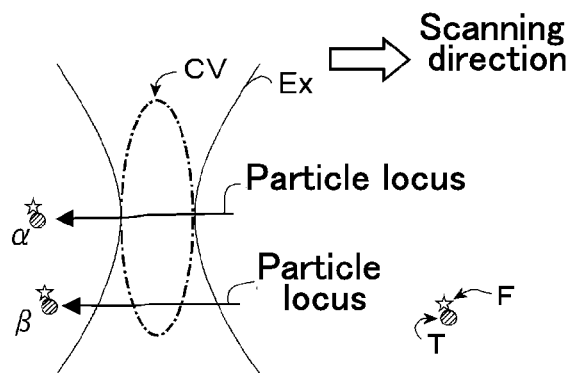
FIG. 4A is a drawing of a model in the case that particles as the object of observation are passing across a light detection region by moving the position of the light detection region in a sample solution at a speed higher than the speed of diffusional movement of the particles as the object of observation.
Figure 4B:
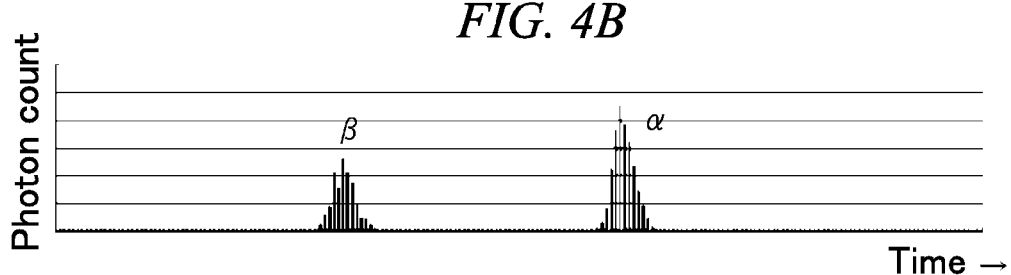
FIG. 4B is a diagram showing an example of the chronological change of the photon counts (light intensity) in FIG. 4A.
Figure 6A:
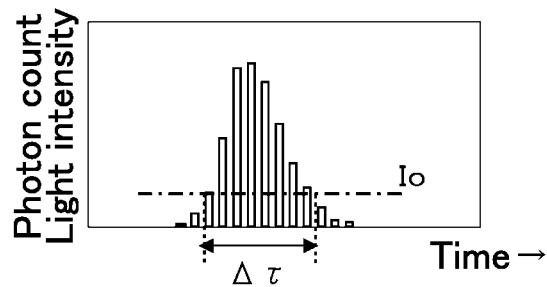
FIG. 6A is a drawing schematically showing the change of the light intensity corresponding to a particle as the object of observation.

When the track of one particle as the object of observation in its passing through the light detection region is approximately straight as shown in FIG. 4A, the change of the light intensity corresponding to the particle in the chronological light intensity data has a profile reflecting the light intensity distribution in the light detection region (determined by the optical system) (usually, an approximately bell shape) as schematically drawn in FIG. 6A. Then, in one of the methods for the detection of a particle as the object of observation, the setting may be such that a threshold value Io is set for the light intensity, and when the time width $\Delta \tau$ for which the light intensity exceeding the threshold value continues is in a predetermined range, the profile of the light intensity may be judged to correspond to one particle having passed through the light detection region, and thereby one particle as the object of observation is detected. The threshold value Io for the light intensity and the predetermined range for the time width $\Delta \tau$ are determined based on a profile expected as the intensity of the light emitted from a combined body of a particle as the object of observation and a luminescent probe (or a luminescent probe having been freed from a particle by decomposition after being bound thereto) moving relatively to the light detection region at a predetermined speed. Their concrete values may be set arbitrarily or experimentally, and also may be selectively determined depending upon the characteristics of a combined body of a particle as the object of observation and a luminescent probe (or a luminescent probe having been freed from a particle by decomposition after being bound thereto).

Moreover, in another method of detection of the particle as the object of observation, the setting may be such that, when the light intensity distribution in the light detection region can be assumed as a Gaussian distribution:

$$I = A \cdot \exp(-2t^2/a^2) \qquad (4)$$

and when the intensity A and the width a, calculated by fitting the expression (4) to the profile of a significant light intensity (a profile which can be clearly judged not to be a background), are within the respective predetermined ranges, the profile of the light intensity may be judged to correspond to one particle as the object of observation having passed through the light detection region, and thereby the detection of one particle as the object of observation will be done. On the other hand, the profile with the intensity A and the width a out of the predetermined ranges may be disregarded as a noise or a contaminant in the analysis.

(ii) The Counting of Particles as the Object of Observation

The counting of particles as the object of observation may be done by counting in an arbitrary way the number of the particles detected by the above-mentioned method of detection of the particle as the object of observation (procedure for counting the number of luminescent particles). However, for a large number of particles, for example, it may be accomplished by the processes illustrated in FIG. 5 and FIG. 6B.

Figure 5:
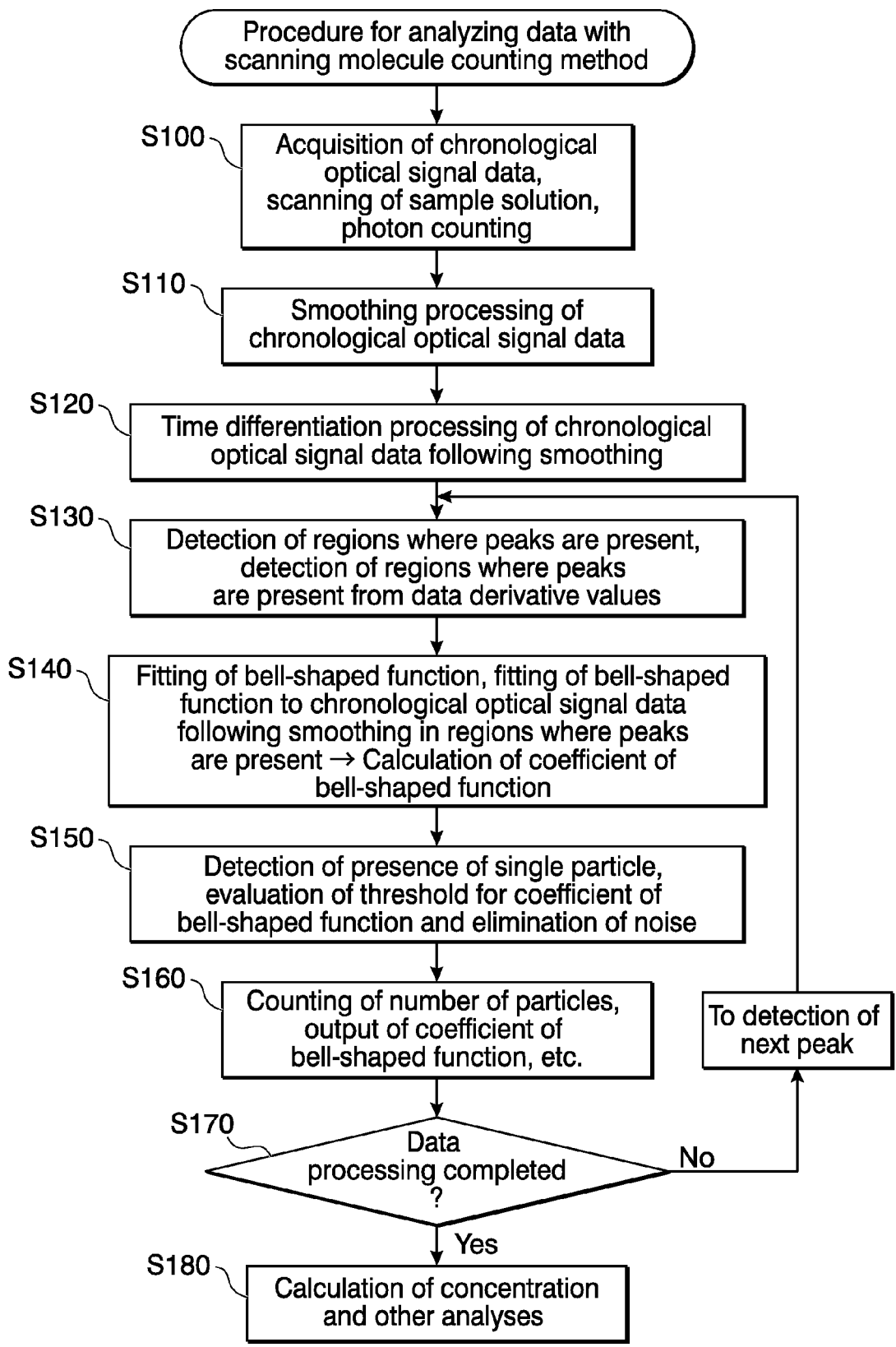
FIG. 5 is a flow chart showing the procedure of processes for counting the particles from the timewise change of the photon counts (light intensity) measured by the scanning molecular counting method.
Figure 6B:
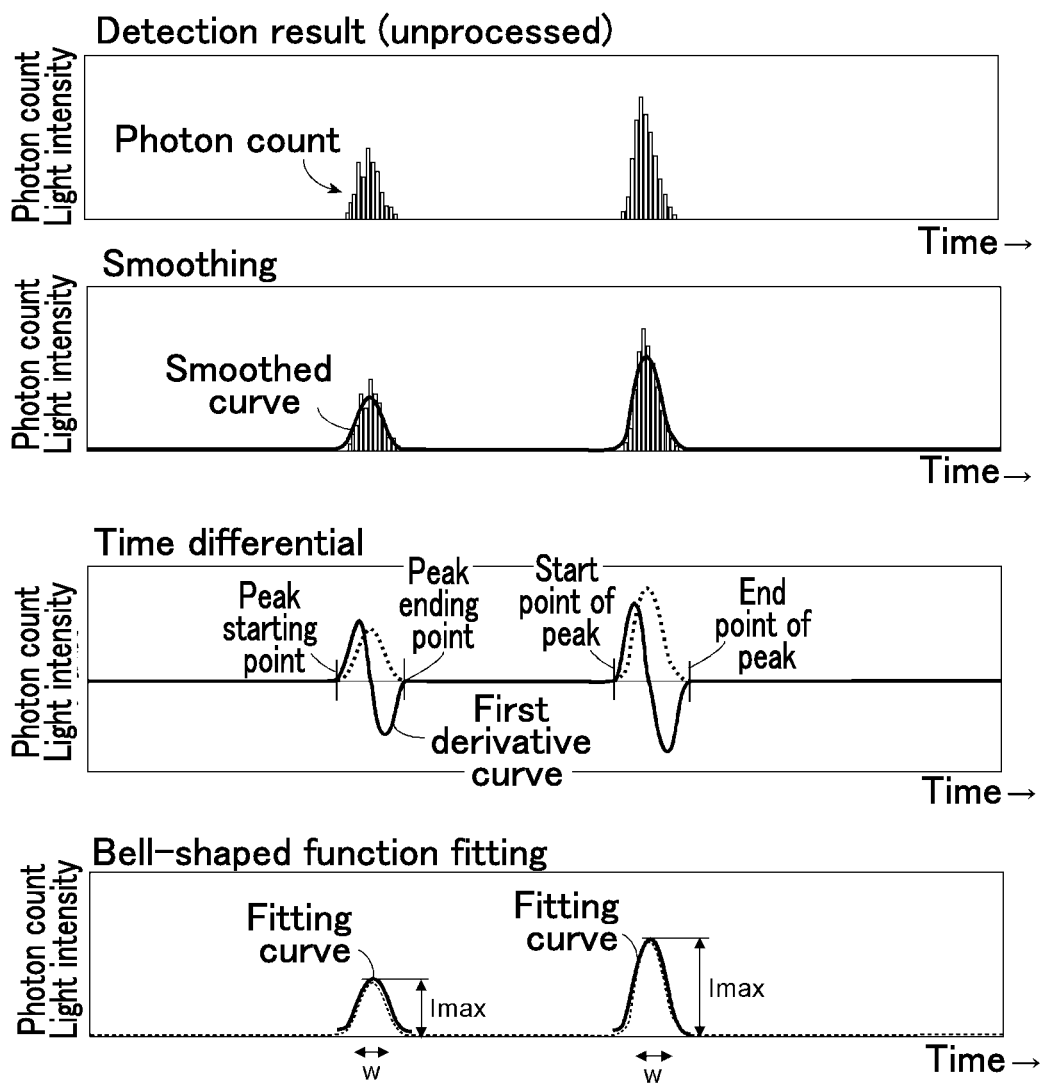
FIG. 6B are drawings explaining examples of the signal processing of the detected signals in the procedure of processes for the counting the particles from the chronological change of the photon counts (light intensity) measured by the scanning molecular counting method.

Referring to FIG. 5 and FIG. 6B, in one example of ways of performing the counting of particles from the chronological light intensity (photon counts) data, after the measurement of the light intensity as explained above, that is, the scanning in the sample solution with the light detection region and the photon counting to acquire chronological light signal data (photon count data) (Step 100), a smoothing process is performed on these chronological light signal data (the upper row "detection result (unprocessed)" in FIG. 6B) (Step 110, mid-upper row "smoothing" in FIG. 6B). Although the light emitted by a combined body of a particle and a luminescent probe, or a luminescent probe, is stochastic so that gaps will be generated in data values in minute times, such gaps in the data values can be disregarded by the smoothing process. The smoothing process may be done, for example, by the moving average method. In this regard, parameters in executing the smoothing process, e.g., the number of datum points in one time of the averaging, the number of times of moving average, etc. in the moving average method, may be suitably set in accordance with the moving speed (scanning speed) of the position of the light detection region and/or BIN TIME in the light signal data acquisition.

Next, on the chronological light signal data after the smoothing process, in order to detect a time domain in which a significant signal exists (peak existence region), the primary differentiation value with time of the chronological light signal data after the smoothing process is computed (Step 120). As illustrated in the mid-low row "time differential" in FIG. 6B, the change of the value increases at the time when the signal value changes in the time differential value of chronological light signal data. Thereby, the start point and the end point of a significant signal (peak signal) can be determined advantageously by referring to the time differential value.

Figure 7:
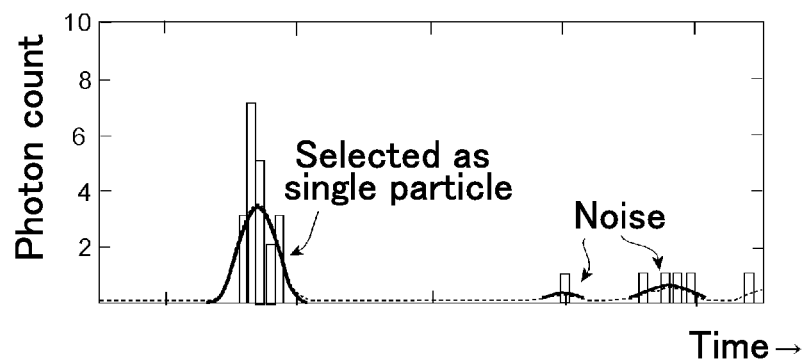
FIG. 7 shows an example of the photon count data measured by the scanning molecular counting method (bar graph), a curve obtained by smoothing the data (dotted line), and gauss functions fitted on the peak existence regions (solid line).

After that, a significant signal (peak signal) is detected successively on the chronological light signal data, and it is judged whether or not the detected peak signal is a signal corresponding to a particle as the object of observation. Concretely, first, on the chronological time-differential value data of the chronological light signal data, the starting point and the end point of one peak signal are searched and determined by referring to the time differential value successively, by which a peak existence region is specified (Step 130). When one peak existence region has been specified, the fitting of a bell-shaped function is applied to the smoothed chronological light signal data in the peak existence region (the lower row "bell-shaped function fitting" in FIG. 6B). Then, parameters in the bell-shaped function, such as the peak intensity, Imax; the peak width (full width at half maximum), w; the correlation coefficient in the fitting (of the least square method), etc. are calculated (Step 140). In this regard, although the bell-shaped function to be used in the fitting is typically a Gauss function, it may be a Lorentz type function. Then, it is judged whether or not the calculated parameters of the bell-shaped function are within the respective ranges assumed for the parameters of the bell-shaped profile drawn by a light signal detected when one combined body of the particle and the luminescent probe, or one luminescent probe, passes through a light detection region, i.e., whether or not the peak intensity, the peak width, and the correlation coefficient are respectively within the predetermined ranges (Step 150). Thus, the signal, whose calculated parameters of the bell-shaped function are judged to be within the ranges assumed in a light signal corresponding to one combined body of the particle and the luminescent probe, or one luminescent probe, as shown in FIG. 7 left, is judged as a signal corresponding to one particle as the object of observation. Thereby, one particle as the object of observation has been detected, and it is counted as one particle (the number of particles is incremented by one: Step 160). On the other hand, a peak signal (signal appended as "noise"), whose computed parameters of the bell-shaped function are not within the assumed ranges, as shown in FIG. 7 right, is disregarded as noise or a contaminant.

The search and the judgment of a peak signal in the processes of the above-mentioned steps 130 to 160 are repetitively executed in the whole region of the chronological light signal data, and whenever one particle as the object of observation is detected, it is counted as one particle. And, when the search of the peak signal in the whole region of the chronological light signal data is completed (Step 170), the count value of particles obtained till then is considered as the number of particles as the object of observation chronological detected light signal data.

(iii) Determination of the Number Density or Concentration of Particles as the Object of Observation When the counting of particles as the object of observation has been done, the number density or concentration of the particle as the object of observation is determined by using the whole volume of the region which the light detection region has passed through during the acquisition of the time series light signal data. However, the effective volume of the light detection region varies depending on the wavelength of excitation light or detected light, the numerical aperture of lenses, and the adjustment condition of the optical system, and therefore, it is generally difficult to compute the effective volume of the light detection region from the design parameter values. Accordingly, it is not easy to compute the whole volume of the region which the light detection region has passed through, either. Then, typically, the light intensity measurement, the detection of particles, and the counting thereof are performed as described above with a solution having a known concentration of the particles (reference solution) under the same condition as that for the measurement of a sample solution to be tested. From the detected number of the particles and the concentration of the particles in the reference solution, the whole volume of the region which the light detection region has passed through, i.e., the relation between the detected number and the concentration of the particles as the object of observation, may be determined The particle of the reference solution may be a light emitting label (fluorescent dye etc.) having the same emission characteristics as those of a combined body of a particle and a luminescent probe, forming the particle as the object of observation (or a luminescent probe freed from the particle as the object of observation after being bound thereto). Concretely, for example, supposing the detected number of the particles is N in a reference solution having a particle concentration C, the whole volume Vt of the region which the light detection region has passed through is given by:

$$Vt = N/C \qquad (5)$$

Alternatively, a plurality of solutions having different concentrations may be prepared as the reference solutions and the measurement may be executed for each of the solutions, and then, the average value of the computed Vt may be employed as the whole volume Vt of the region which the light detection region has passed through. Thus, when Vt is given, the number density c of the particles of the sample solution, whose counting result of the particles is n, is given by:

$$c = n/Vt \quad (6)$$

In this regard, the volume of the light detection region and the whole volume of the region which the light detection region has passed through may be given by an arbitrary method, for instance, using FCS and FIDA, instead of the above-mentioned method. Moreover, in the photometric analysis device of this embodiment, the information on the relations (expression (5)) between the concentrations C and the numbers N of various standard particles for assumed moving patterns of the light detection region may be previously stored in a storage device of the computer 18, so that a user of the device can appropriately use the stored information on the relation in conducting photometric analysis.

<Quantitative Determination Method for Target Particles>

The quantitative determination method for target particles according to one embodiment of the present invention is a method for quantifying target particles which are dispersed and moving at random in a sample solution, wherein the method comprises: labeling the target particles in the sample solution by binding with luminescent probes; and thereafter, calculating the concentration of the target particles in this sample solution from the number of the target particles bound to the luminescent probes counted by the scanning molecular counting method, on the basis of a calibration curve formed by using a standard sample having a known concentration of the target particles (concentration calculation procedure). Since the scanning molecular counting method is a measurement method capable of measuring luminescent particles by each particle in a condition where molecules are spaced and apart from each other, the measurement is possible for luminescent particles whose concentration is relatively low in a pM order or lower. For this reason, with the quantitative determination method for target particles according to one embodiment of the present invention, even if the concentration of target particles as the object of analysis in a sample solution is extremely low, the target particles can be counted with good sensitivity. Furthermore, in the quantitative determination method for target particles according to one embodiment of the present invention, although the target particles are detected through the binding with the luminescent probes, the concentration of the target particles in the sample solution can be obtained more simply and readily because a calibration curve is used.

In addition, the quantitative determination method for target particles may also include a procedure for determining the number density or concentration of the luminescent particles in the sample solution, on the basis of the number of the detected luminescent particles.

Specifically, the quantitative determination method for target particles according to one embodiment of the present invention has the following steps (a) to (c):

(a) preparing a sample solution containing the target particles and luminescent probes to be bound to the target particles, and binding the target particles and the luminescent probes in the sample solution;

(b) counting the number of the target particles existing in the solution prepared in the (a); and (c) calculating the concentration of the target particles in the sample solution from the number of the counted target particles, on the basis of a calibration curve that approximates the correlation between the concentration or quantity of the target particles in the sample solution and the number of the target particles.

Furthermore, the (b) comprises moving a position of a light detection region of the optical system in the sample solution, with use of an optical system of a confocal microscope or a multiphoton microscope, and detecting a light signal emitted from the luminescent probe in the light detection region, and individually detecting the target particles while moving the position of the light detection region of the optical system in the sample solution. Hereunder is a description of respective steps.

First, as the (a), a sample solution containing target particles and luminescent probes to be bound to these target particles, is prepared, and the target particles and the luminescent probes are bound to each other in this sample solution.

In one embodiment of the present invention, "a particle dispersed and moving at random in a sample solution" means a particle, such as an atom, a molecule, or an aggregate thereof, (which may be either a particle emitting light or a particle not emitting light) being dispersed or dissolved in a sample solution, and is a particle making Brownian motion freely in the solution without being fixed on a substrate, etc.

The target particle is a particle dispersed and moving at random in a sample solution, and is a particle as an object whose concentration in the sample solution is to be quantified. The target particle may be, for instance, a biological molecule, i.e. a protein, a peptide, a nucleic acid, a nucleic acid analog, a lipid, a sugar chain, an amino acid, etc. or an aggregate thereof, a biological object in a particulate form, i.e. a virus, a cell, etc. or a non-biological particle (i.e., an atom, a molecule, a micelle, a metallic colloid, etc.). The nucleic acid may be DNA, RNA, or an artificially amplified polymer such as cDNA.

The nucleic acid analog can be exemplified by substances in which a side chain etc. of a natural nucleotide (a nucleotide which exists in nature) such as DNA or RNA is modified with a functional group such as an amino group etc., substances labeled with a protein, a low molecular compound, etc., and the like. More concretely, the examples include bridged nucleic acid (BNA), a nucleotide in which an oxygen atom at the 4' position of a natural nucleotide is substituted with a sulfur atom, a nucleotide in which a hydroxyl group at the 2' position of a natural ribonucleotide is substituted with a methoxy group, a hexitol nucleic acid (HNA), a peptide nucleic acid (PNA), and the like.

Moreover, the luminescent probe for use in one embodiment of the present invention is not particularly limited as long as it is a substance which can be specifically or non-specifically bound or adsorbed to the target particle, and is a substance whose emission characteristic of emitted light is different between the binding state to the target particle and the solely existing state. For example, a luminescent substance may be bound to a substance which can be specifically or non-specifically bound or adsorbed to the target particle. The luminescent substance is typically a fluorescent substance, although it may be a substance which emits light by phosphorescence, chemiluminescence, bioluminescence, light scattering, etc. The fluorescent substance is not particularly limited as long as it is a substance which emits fluorescence by irradiation of light of a specific wavelength, and may be used by appropriately selecting from fluorescent dyes for use in FCS, FIDA, and the like.

For example, when the target particle is a nucleic acid or a nucleic acid analog, the luminescent probe can be exemplified by a substance in which a luminescent substance such as a fluorescent substance is bound to an oligonucleotide which is hybridizable with the target particle, a nucleic acid-binding protein to which a luminescent substance such as a fluorescent substance is bound, a dye molecule which can be bound to a nucleic acid, and the like. This oligonucleotide may be DNA, RNA, or an artificially amplified polymer such as cDNA, a part or all of which may include a nucleotide chain or a nucleic acid analog which is capable of forming base pairs, similarly to natural nucleic acid bases. Moreover, when the target particle is a protein, then an antigen or an antibody for the target particle, a ligand or a receptor for the target particle, or a substance, which are labeled with a luminescent substance such as a fluorescent substance, can be used as the luminescent probe. The binding of a luminescent substance to the substance such as a nucleic acid or a protein which can be specifically or non-specifically bound or adsorbed to the target particle, can be performed by a usual method.

The luminescent probe for use in one embodiment of the present invention may be a substance which can be non-specifically bound etc. to the target particle, although a substance which can be specifically bound etc. thereto is preferred in terms of the precision of the detection/quantification of the target particles. The luminescent probe which can be specifically bound to the target particle may be a substance which can be preferentially bound to the target particle rather than to another substance whose physical or chemical characteristics are similar to those of the target particle, and it is not necessary to be a substance which would not be bound to any other substance than the target particle at all. For example, when the target particle is a nucleic acid, an oligonucleotide labeled with a luminescent substance for use as a luminescent probe may have a base sequence which is completely complementary to the base sequence of the target particle, or may have a base sequence which has mismatch(es) against the base sequence of the target particle.

Moreover, the phrase "emission characteristics of the luminescent probe is different between the binding state to the target particle and the solely existing state" means that the intensity of light of a specific wavelength is different between the state in which the luminescent probe is bound to the target particle and the state in which the luminescent probe solely exists. By making a difference in the intensity of light of a specific wavelength between the state in which the luminescent probe solely exists and the state in which the luminescent probe is bound to the target particle (for example, making a difference in the fluorescence intensity), both states can be detected distinctively in the scanning molecular counting method.

When the target particle is a protein, a dye whose fluorescence intensity or fluorescence wavelength is changed by a change of the surrounding environment due to the binding to the protein (for example, a hydrophobic probe, ANS, MANS, TNS, or such a fluorescent dye), can be used as the luminescent probe. Moreover, the luminescent probe may not need to emit light by itself. For example, when the target particle is a nucleic acid or a nucleic acid analog, an oligonucleotide which is hybridizable with the target particle is used as the luminescent probe, and a fluorescent double stranded nucleic acid-binding substance which can be specifically bound to a double stranded chain structure is added together with this luminescent probe in a sample solution. By so doing, a difference in the emission characteristics can be made between the state in which the luminescent probe solely exists (non-binding state) and the state in which the luminescent probe is bound to the target particle (binding state). As the fluorescent double stranded nucleic acid-binding substance which can be specifically bound to a double stranded chain structure, there can be exemplified a fluorescent intercalator, a group binder bound with a fluorescent substance, and the like.

Besides, for example, a substance composed of at least two components as well as being a substance which emits fluorescence by a change in the mutual positions of these at least two components due to the binding to the target particle, may be employed as the luminescent probe. Such a substance can be exemplified by a fluorescent protein which emits strong fluorescence by a change in the structure when being bound to a certain particle, and a molecule (ligand of a complex) which forms a fluorescent metal complex by assembling when being bound to a certain particle. According to this structure, in any case, the luminescent probe as a single body or the luminescent probe not bound to the target particle emits almost no light, or even if it emits light, it has a different wavelength from that of the combined body of the target particle and the luminescent probe, by which it becomes possible to selectively detect light from the combined body of the target particle and the luminescent probe.

In addition, by utilizing the fluorescence energy transfer phenomenon (FRET), a difference can be made in the emission characteristics between the luminescent probe solely existing in a sample solution and the luminescent probe in the binding state to the target particle. For example, a fluorescent substance serving as an energy donor and a substance serving as an energy acceptor in FRET (a fluorescent substance and a quencher substance) are bound to a substance which can be bound to the target particle to achieve a condition where FRET occurs in the state where the luminescent probe solely exists and FRET does not occur in the binding state to the target particle. By so doing, the substance as a result of this binding can be used as a luminescent probe. FRET does not occur from the luminescent probe bound to the target particle, and therefore fluorescence is emitted from the fluorescent substance serving as an energy donor. On the other hand, fluorescence to be emitted from the fluorescent substance serving as an energy donor is not detected or attenuated from the solely existing luminescent probe. Therefore, by detecting the fluorescence emitted from the fluorescent substance serving as an energy donor, the target particle bound to the luminescent probes can be detected distinctively from the solely existing luminescent probe.

For example, when the target particle is a nucleic acid or a nucleic acid analog, a molecular beacon probe is made by binding a fluorescent substance serving as an energy donor and a substance serving as an energy acceptor in FRET, to an oligonucleotide which forms an intramolecular structure in a state of a single stranded nucleic acid molecule, to achieve a condition where FRET occurs in a state of a single stranded nucleic acid molecule and FRET does not occur in a state of an associated body formed by hybridization with a different single stranded nucleic acid molecule. This molecular beacon probe may be used as the luminescent probe. In one embodiment of the present invention, preferred is a substance in which a fluorescent substance serving as an energy donor or a substance serving as an energy acceptor is bound to the 3'-end side and the other is bound to the 5'-end side, as well as having mutually complementary base sequences in regions on the sides of the 3'-end and the 5'-end, and which forms an intramolecular structure by forming base pairs between these base sequences (a so-called stem loop structure). The mutually complementary regions which form the intramolecular base pairs of the molecular beacon probe may exist so as to interpose the region which is hybridizable with the target particle, and the regions on the sides of the 3'-end and the 5'-end may or may not be regions respectively including the 3'-end or the 5'-end. Moreover, the numbers of bases and the base sequences of the regions forming the base pairs may be at degrees where the stability of the formed base pairs is lower than the stability of the associated body with the target particle, and where the base pairs can be formed under the measurement condition.

Moreover, using a fluorescent double stranded nucleic acid-binding substance which can be specifically bound to a double stranded structure, it is also possible, by causing FRET between this fluorescent double stranded nucleic acid-binding substance and the luminescent probe-labeled fluorescent substance, to distinguish the solely existing luminescent probe and the luminescent probe bound to the target particle. That is, either one of the fluorescent double stranded nucleic acid-binding substance or the fluorescent substance for labeling the luminescent probe serves as an energy donor of FRET, and the other one serves as an energy acceptor of this FRET. From the solely existing luminescent probe, fluorescence to be emitted from the fluorescent substance for labeling this luminescent probe is detected. On the other hand, since the fluorescent double stranded nucleic acid-binding substance is bound to the luminescent probe being bound to the target particle, fluorescence to be emitted from FRET is detected from the combined body. As a result, the combined body can be detected distinctively from the solely existing luminescent probe.

If the amount of the fluorescent intercalator to be inserted between the base pairs of the associated body of the luminescent probe and the target particle is too large, the background for detecting the fluorescence emitted from FRET becomes so high that the detection precision might be influenced. For this reason, it is preferable to design the luminescent probe so that the region forming the double strand in the associated body of the luminescent probe and the target particle is 400 bp or shorter.

Besides, in one embodiment of the present invention, two types of luminescent probes may be used. For example, two types of luminescent probes are designed so that, when the target particle is a nucleic acid or a nucleic acid analog, they can be hybridized with the target particle in mutually adjacent positions. Then, one luminescent probe is labeled with a fluorescent substance serving as an energy donor in FRET, and the other luminescent probe is labeled with a substance serving as an energy acceptor in this FRET. In this case, FRET does not occur in the solely existing luminescent probes. However, when they are bound to the target particle, these two types of luminescent probes become mutually adjacent (for example, the distance between these two types of luminescent probes is about 1 to 10 nm) and thus FRET occurs. For this reason, the target particle can be detected by detecting fluorescence to be emitted from this FRET.

Concretely, in the (a), firstly, target particles and luminescent probes are added to an appropriate solvent to prepare a sample solution. This solvent is not particularly limited as along as it is a solvent which does not interfere with the detection of light emitted from the luminescent probes, and the detection of the luminescent probes by the scanning molecular counting method, and the solvent can be used by appropriately selecting from buffers for usual use in this technical field. This buffer can be exemplified by phosphate buffers such as PBS (phosphate buffered saline, pH 7.4), Tris buffer, and the like.

If the target particle and the luminescent probe can be bound to each other only by having them coexist in the same solution, the target particle and the luminescent probe can be bound to each other in this sample solution only by incubating this sample solution for a predetermined period of time as required after the preparation of the sample solution.

On the other hand, if the target particle and the luminescent probe are a nucleic acid or a nucleic acid analog having a double stranded structure, it is preferable to make them associate with each other after denaturing the nucleic acid etc. in the sample solution. The term "to denature a nucleic acid or a nucleic acid analog" means to dissociate the base pairs. For example, it means to dissociate the base pairs formed by the mutually complementary base sequences in a molecular beacon probe to open the intramolecular structure to be in a single stranded structure, or to separate a double stranded nucleic acid molecule into single stranded nucleic acid molecules. If the luminescent probe is an oligonucleotide including a nucleic acid analog such as PNA, it may be possible in some cases to form an associated body composed of this luminescent probe and the target particle without performing a special denaturation treatment, even if the target particle is a double stranded nucleic acid molecule.

The denaturation treatment can be exemplified by denaturation by means of a high temperature treatment (heat denaturation), denaturation by means of a low salt concentration treatment, and the like. Of these, it is preferable to perform heat denaturation because the influence to the luminescent substance such as a fluorescent substance is relatively low, and the manipulation is simple. Concretely, heat denaturation is capable of denaturing a nucleic acid or the like in this sample solution by treating this sample solution with high temperature. Generally, the denaturation can be done by keeping the temperature at 90° C. for DNA and 70° C. for RNA for about several seconds to two minutes, although the temperature for the denaturation is multifarious depending on the base length of the target particle etc., and it is not to be limited to this temperature as long as the denaturation is possible. On the other hand, the denaturation by means of a low salt concentration treatment can be performed by adjustment by means of dilution with, for example, purified water or the like, so that the salt concentration of this sample solution can be sufficiently low.

After the denaturation as required, the target particle and the luminescent probe in the sample solution are associated with each other. If the heat denaturation is performed, the target particle and the luminescent probe in this sample solution can be suitably associated with each other by lowering the temperature of this sample solution to a temperature at which both parties can specifically hybridize with each other, after the high temperature treatment. Moreover, if the denaturation by means of a low salt concentration treatment is performed, the target particle and the luminescent probe in this sample solution can be suitably associated with each other by raising the salt concentration of this sample solution to a concentration at which both parties can specifically hybridize with each other, by adding a salt solution or the like.

The temperature at which two single stranded nucleic acid molecules can specifically hybridize with each other can be obtained from the melting curve of the associated body composed of both parties. The melting curve can be obtained by, for example, changing the temperature of a solution containing only both parties from a high temperature to a low temperature, and measuring the absorbance or the fluorescence intensity of this solution. From the obtained melting curve, a temperature within a range from the temperature at which the two denatured single stranded nucleic acid molecules start to form an associated body to the temperature at which almost all the molecules have formed associated bodies, can be set as the temperature at which both parties can specifically hybridize with each other. Instead of the temperature, the concentration at which two single stranded nucleic acid molecules can specifically hybridize with each other can be obtained by determining the melting curve by changing the salt concentration in the solution from a low concentration to a high concentration in the same manner.

The temperature at which two single stranded nucleic acid molecules can specifically hybridize with each other can be generally substituted with a Tm value (melting temperature). For example, the Tm value of the region which is hybridizable with the target particle (the temperature at which 50% of double stranded DNA is dissociated into single stranded DNA) can be calculated from the base sequence information of the luminescent probe by using a usual primer/probe design software etc.

Moreover, it is preferable to relatively slowly lower the temperature of the sample solution for forming the associated body so as to suppress non-specific hybridization. For example, after denaturing the nucleic acid molecules by setting the temperature of the sample solution at 70° C. or higher, the liquid temperature of this sample solution can be lowered at a cooling rate of 0.05° C./sec. or quicker.

In addition, so as to suppress non-specific hybridization, it is also preferable to previously add a surfactant, formamide, dimethyl sulfoxide, urea, or the like, in the sample solution. A single type of, or a combination of two or more types of, these compounds may be added. By adding these compounds, non-specific hybridization can be less likely to occur under a relatively low temperature environment.

Thereafter, as the (b), the number of the target particles in the prepared sample solution is counted by the scanning molecular counting method. Concretely, the sample solution after the target particles have been bound to the labeling probes is set in the above-mentioned photometric analysis device for the scanning molecular counting method, and light emitted from the labeling probes is detected and analyzed by the above-mentioned technique. By so doing, the number of the target particles is calculated.

After the (a), as the (d), the luminescent probe which is not bound to the target particle is separated from the sample solution, and a complex is collected. In the method of one embodiment of the present invention using the photometric analysis technique for individually detecting the target particle labeled with the luminescent probe, if light from the luminescent probe such as a free luminescent probe which is not bound to the target particle is detected not distinctively from light from the luminescent probe, the detection precision of the target particle would be deteriorated. Therefore, in the (d), the luminescent probe such as a free luminescent probe which is not bound to the target particle is removed from the complex.

The method for separating a luminescent probe which is not bound to the target particle and collecting the complex is not particularly limited, and may be performed by appropriately selecting from substance separation methods which are usually performed in this technical field for physically separating a plurality of substances by utilizing the difference in the size or the molecular weight, the affinity for an arbitrary substance, the charged state, and the like. The separation method can be exemplified by operations including adsorption/extraction or washing. Concretely, chromatography (hydrophilic/hydrophobic chromatography, affinity chromatography, ion exchange chromatography, and the like), ultrafiltration, electrophoresis, phase separation, centrifugal separation, solvent extraction, filter adsorption, and the like, can be enumerated.

It is also possible to collect the complex by separating from the luminescent probe which is not bound to the target particle by utilizing a separation probe which can bind to the target particle independently from the luminescent probe. Concretely, in (a), the separation probe is additionally added to the sample solution to form a complex including the target particle, the luminescent probe, and the separation probe. Next, in the (d), the complex is collected by separating from the luminescent probe which is not bound to the target particle by utilizing the interaction between the separation probe in the complex and another substance.

The separation probe is not particularly limited as long as it is a substance which can be specifically or non-specifically bound or adsorbed to the target particle independently from the luminescent probe. The separation probe may be bound to the target particle indirectly via another substance, although preferred is a probe which can be directly bound to the target particle. The substance which can be used as the separation probe, that is, a probe which can be specifically or non-specifically bound or adsorbed directly to the target particle is the same as those enumerated as the luminescent probe before being bound to the luminescent substance. For example, an oligonucleotide which is hybridizable with the target particle can be exemplified when the target particle is a nucleic acid molecule or a nucleic acid analog; and an antigen or an antibody for the target particle, or a ligand or a receptor for the target particle can be exemplified, when the target particle is a protein.

As the separation probe for use in one embodiment of the present invention, preferred is a probe which has a site to bind to a solid-phase carrier, and furthermore, which can bind to the solid-phase carrier directly or indirectly in a binding state to the target particle. When using such a separation probe, it is possible to more simply collect the complex in the (d), and to collect the free luminescent probe in the following (e), by a solid-liquid separation treatment using the solid-phase carrier which can bind to the separation probe directly or indirectly.

The shape, the material, etc. of the solid-phase carrier is not particularly limited as long as it is a solid having a site to bind to the separation probe. For example, the solid-phase carrier may be particles, such as beads, which can be suspended in water and can be separated from liquid by a general solid-liquid separation treatment, a membrane, a container, a chip substrate, or the like. Concretely, the solid-phase carrier can be exemplified by magnetic beads, silica beads, agarose gel beads, polyacrylamide resin beads, latex beads, plastic beads such as polystyrene beads, ceramic beads, zirconia beads, a silica membrane, a silica filter, a plastic plate, and the like.

For example, when the separation probe is an oligonucleotide, then beads or a filter the surface of which is bound with an oligonucleotide which is hybridizable with a region in the oligonucleotide other than the region which is hybridizable with the target particle, can be used as a solid-phase carrier. Moreover, when the separation probe has biotin as a site to bind to the solid-phase carrier, then beads or a filter the surface of which is bound with avidin or streptavidin can be used as a solid-phase carrier. In addition, when the site in the separation probe to bind to the solid-phase carrier is glutathione, dinitorophenol (DNP), digoxigenin (Dig), digoxin, a sugar chain consisting of two or more sugars, a polypeptide consisting of four or more amino acids, auxin, gibberellin, a steroid, a protein, a hydrophilic organic compound, and an analog thereof, etc., then beads or a filter the surface of which is bound with an antibody, an antigen, a ligand, or a receptor for these substances can be used as a solid-phase carrier. The solid-phase carrier may be non-specifically bound etc. to the separation probe, although it is preferable that the carrier can be specifically bound etc. thereto in terms of the precision of the detection/quantification of the target particles.

Concretely, by contacting the solid-phase carrier to the sample solution and incubating this sample solution as required, the complex including the target particle, the luminescent probe, and the separation probe in this sample solution is bound to the solid-phase carrier via the separation probe in the complex. Thereafter, by performing the solid-liquid separation treatment, the complex bound to the solid-phase carrier can be collected separately from the luminescent probe which is not bound to the target particle existing in the liquid phase, such as a free luminescent probe.

The solid-liquid separation treatment is not particularly limited as long as it is a method capable of collecting the solid-phase carrier in the sample solution separately from the liquid component, and can be used by appropriately selecting from known treatments for use in solid-liquid separation treatments. For example, when the solid-phase carrier consists of particles such as beads, a centrifugal separation treatment may be applied to the suspension containing the solid-phase carrier so as to precipitate the solid-phase carrier, and the supernatant may be removed. Moreover, the sample solution may be filtrated by using a filter paper or a filtration filter, and the solid-phase carrier remaining on the surface of the filter paper etc. may be collected. In addition, when the solid-phase carrier consists of magnetic beads, a magnet may be brought closer to a container containing the sample solution to gather the solid-phase carrier to the surface of the container which is the closest to the magnet, and then the supernatant may be removed. When a container the inner wall of which is covered with a substance to bind to the separation probe is the solid-phase carrier, the sample solution containing the complex is poured in the container and incubated as required, and then the liquid in the container is discharged. Note that, when the solid-phase carrier is a membrane or a filter, it is possible, by filtrating the sample solution containing the complex through the solid-phase carrier, to perform the binding of the solid-phase carrier and the complex, and the separation and collection of the complex from the luminescent probe which is not bound to the target particle, in one operation.

In one embodiment of the present invention, it is also possible, in the (a), to previously add the solid-phase carrier together with the target particle, the luminescent probe, and the separation probe, in the sample solution, to form a complex including the target particle, the luminescent probe, and the separation probe which is bound to the solid-phase carrier, and thereafter performing a solid-liquid separation treatment, to thereby separate the complex bound to the solid-phase carrier from the luminescent probe not bound to the target particle, to collect the complex. Moreover, in the (a), the sample solution may be prepared by previously adding the separation probe in a binding state to the solid-phase carrier with the target particle and the luminescent probe. The separation probe to be used in this case may be bound to the solid-phase carrier in a reversible manner or in a non-reversible manner By adding an appropriate solvent to the collected solid-phase carrier, the sample solution containing the complex bound to the solid-phase carrier is prepared. The collected solid-phase carrier is subjected to the (e) as a sample solution containing it. The solvent is not particularly limited as long as it is a solvent which does not interfere with the detection of light emitted from the luminescent probe in the following operation. The solvent can be used by appropriately selecting from buffers for usual use in this technical field. The buffer can be exemplified by a phosphate buffer such as PBS (phosphate buffered saline, pH7.4), Tris buffer, and the like.

The collected solid-phase carrier may also be washed with an appropriate solvent prior to the (e). By washing, the free luminescent probe can be more strictly separated and removed from the complex bound to the solid-phase carrier. The solvent to wash the solid-phase carrier is not limited as long as it does not hinder the binding between the complex and the solid-phase carrier, and may be the same type of solvent for use in the preparation of the sample solution containing the complex bound to the solid-phase carrier to be subjected to the (e), or may be a different type of solvent.

Thereafter, as the (e), the luminescent probe is dissociated from the complex having been collected in the (d), and thereafter the free luminescent probe and the target particle are collected separately from each other.

The method for dissociating the luminescent probe in the complex is not particularly limited as long as it is a method which enables to cancel the binding between the target particle and the luminescent probe in the complex.

For example, when the target particle is an oligonucleotide composed of a nucleic acid molecule or a nucleic acid analog, and the site to bind to the target particle in the luminescent probe is an oligonucleotide composed of a nucleic acid molecule or a nucleic acid analog which is hybridizable with the target particle; then, the temperature of the sample solution containing the complex is raised to be sufficiently higher than the condition for the specific association between the target particle and the luminescent probe, or the salt concentration of the sample solution containing the complex is lowered to be sufficiently lower than the condition for the specific association between the target particle and the luminescent probe. By so doing, the binding between the luminescent probe and the target particle can be cancelled, and thereby the luminescent probe can be dissociated from the complex.

The method for collecting the dissociated luminescent probe, and the target particle as a single body or which forms the complex, separately from each other is not particularly limited, and may be performed by appropriately selecting from substance separation methods which are usually performed in the above-mentioned technical field by considering; the difference in the size between the luminescent probe and the target particle as a single body, or the complex including the target particle, the difference in the affinity for an arbitrary substance, and the like. Concretely, chromatography (hydrophilic/hydrophobic chromatography, affinity chromatography, ion exchange chromatography, and the like), ultrafiltration, electrophoresis, phase separation, centrifugal separation, solvent extraction, filter adsorption, and the like, can be enumerated.

Figure 8:
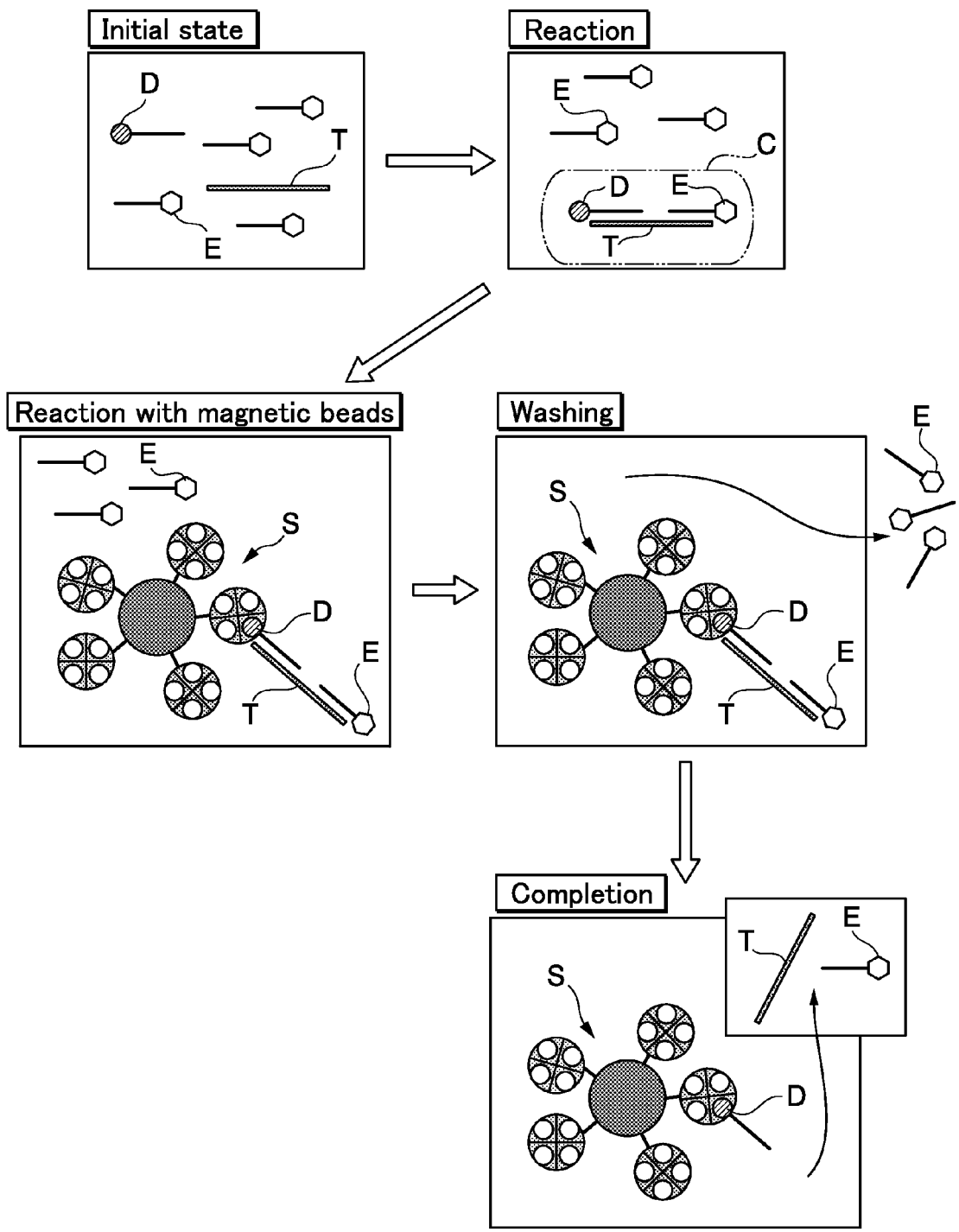
FIG. 8 are drawings schematically showing an embodiment using a separation probe and a solid-phase carrier which binds to the separation probe.

FIG. 8 are drawings schematically showing an embodiment using a separation probe D and a solid-phase carrier S which binds to the separation probe D. Firstly, the target particle T, the luminescent probe E, and the separation probe D are bound to form a complex C. The complex C is bound to the solid-phase carrier S via the separation probe D, and then free luminescent probes E are removed by washing. Thereafter, the luminescent probe E is dissociated from the complex C, and the free luminescent probe E and the target particle T bound to the solid-phase carrier S via the separation probe D are separately collected.

Finally, as the (c), on the basis of a calibration curve that approximates the correlation between the concentration or quantity of the target particles in the solution and the number of the target particles bound to the luminescent probes having been counted from the solution, the concentration of the target particles in the sample solution is calculated from the number of the counted target particles. In one embodiment of the present invention, by using the calibration curve, the concentration of the target particles in the sample solution can be readily obtained from the number of the target particles detected via the luminescent probes.

Concretely, for the calibration curve, firstly, a standard sample series having different concentrations of the target particles is prepared. The standard sample series can be prepared by, for example, stepwise dilution of a solution having a known concentration of the target particles with a solvent such as water, buffer, etc. The number of the standard sample solutions constituting the standard sample series is not particularly limited, and may be from about three to twenty. Moreover, the concentration of the target particles in each standard sample solution is not particularly limited, and can be suitably prepared by considering the type of the target particle, the affinity between the luminescent probe and the target particle, the expected concentration of the target particles in the sample solution to be analyzed, and the like. In the standard sample series, the concentrations of the target particles of respective standard sample solutions may be set to have equal intervals or unequal intervals.

Next, each of the standard sample solutions in the standard sample series is subjected to the (a) and (b) under the same conditions as those for the sample solution to be analyzed, to count the number of the target particles bound to the luminescent probes existing in each standard sample solution. That is, a solution for the measurement is prepared by adding each standard sample solution and the luminescent probes to a solvent of the same type as the sample solution to be analyzed, so that the concentration would be equivalent to that of this sample solution. Then, the same treatment as the (a) is performed to thereby bind the target particle and the luminescent probe in each solution for the measurement. Thereafter, using the same device and the same program as those of the (b), the measurement is performed by the scanning molecular counting method to calculate the number of the target particles bound to the labeling probes. The series of the measurements for each standard sample solution may be performed at substantially the same time as that of the (a) and (b), may be previously performed prior to the (a), or may be performed after the (b).

From the number of the target particles bound to the luminescent probes having been counted for each standard sample solution, and the concentration of the target particles of the standard sample solution, a continuously differentiable function that approximates the relation therebetween can be obtained. The obtained continuously differentiable function is used as the calibration curve. The method for forming the calibration curve is not particularly limited, and it may be formed by using any calculation and analysis method for usual use in the formation of an approximate line of the relation between two types of quantitative data. For example, in a graph where the horizontal axis shows the concentration of the target particles and the vertical axis shows the number of the target particles, data obtained from the respective standard sample solutions are plotted. The calibration curve can be formed by applying the least square method etc. to respective plots. In many cases, a calibration curve similar to a sigmoid curve can be formed by plotting the measured values in a single logarithmic graph where the concentration of the target particles is logarithmically expressed.

<Device and Program of this Embodiment>

Using a device or the like prepared by adding the structure and the procedure for performing the (c) to the photometric analysis device for the scanning molecular counting method and the program for this device, the (b) and (c) can be performed with this device.

Concretely, it is a photometric analysis device for use in the scanning molecular counting method mentioned above, that is, a photometric analysis device for detecting light from luminescent particles dispersed and moving at random in a sample solution, with use of an optical system of a confocal microscope or a multiphoton microscope, wherein the photometric analysis device comprises: a light detection region mover for moving the position of the light detection region of the optical system in the sample solution by changing the optical path of the optical system; a light detector for detecting light from the light detection region; and a signal processor for, while moving the position of the light detection region in the sample solution, individually detecting light signals from the respective ones of the luminescent particles detected in the light detector, and counting the number of the luminescent particles detected during the moving of the position of the light detection region by counting the number of the individually detected light signals from the luminescent particles. Furthermore, the photometric analysis device also comprises: a storage for storing the calibration curve that approximates the correlation between the concentration or quantity of the luminescent particles in the sample solution and the number of the luminescent particles counted from this sample solution; a concentration calculator for, on the basis of the calibration curve, calculating the concentration of the luminescent particles in the sample solution from the number of the luminescent particles counted in the signal processor; and a display for displaying the concentration of the luminescent particles in the sample solution calculated by the concentration calculator.

For example, the computer 18 may comprises the signal processor, the storage, and the concentration calculator mentioned above.

Figure 9:
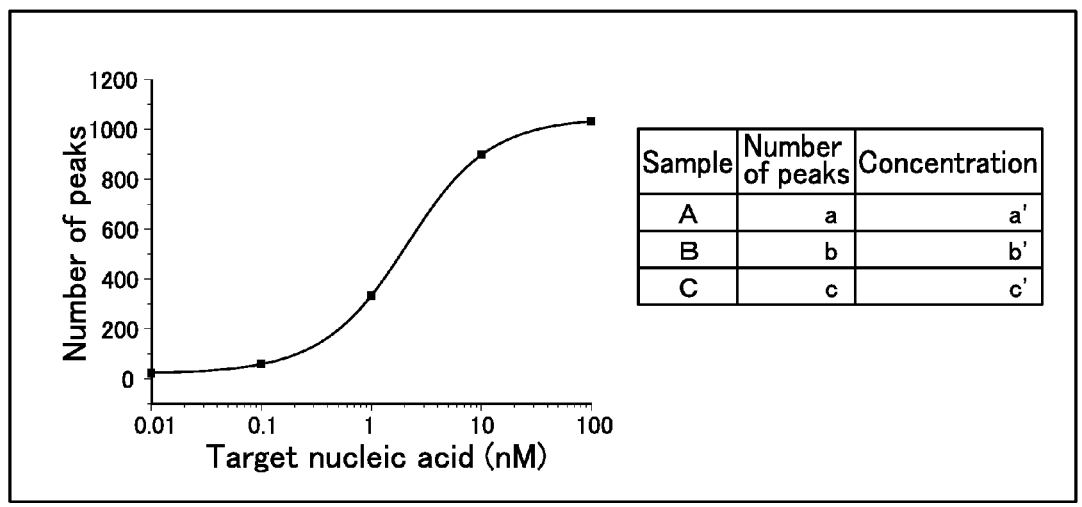
FIG. 9 is a drawing showing an embodiment of the data displayed in the display of the device according to one embodiment of the present invention.
Figure 10:
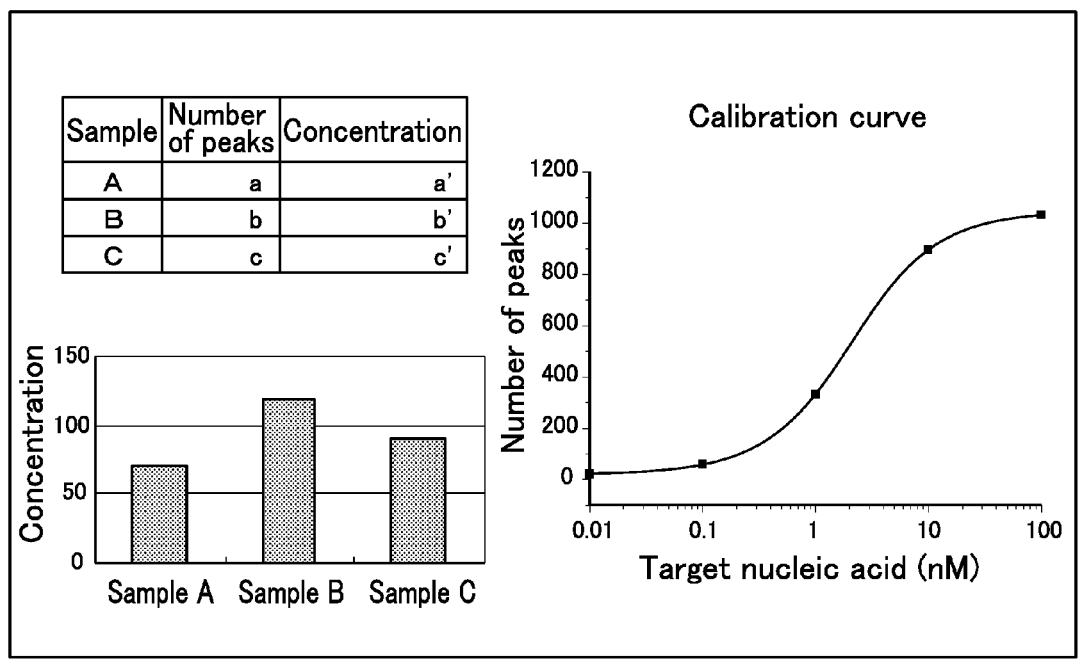
FIG. 10 is a drawing showing another embodiment of the data displayed in the display of the device of the present invention.

In the display, the concentration of the luminescent particles in the sample solution having been calculated from the calibration curve is displayed irrespective of the format such as the numerical value, table, graph, etc. Moreover, it is also preferable that the calibration curve itself and the number of the luminescent particles counted in the signal processor are displayed. FIG. 9 and FIG. 10 each show an embodiment of the data displayed in this display. Besides, in this display, the conditions for detecting light from the light detection region (the amount of the sample solution, the temperature of the environment at the time of the measurement, the wavelength or intensity of light emitted from the optical system, the position of the light detection region, the speed of moving the position of the light detection region at the time of the acquisition of the light signal data (scanning speed) etc.) may also be displayed. As this display, a known image display device such as a liquid crystal display etc. may be used.

For example, the (b) and (c) can be performed by a device comprising the photometric analysis device as shown in FIG. 1 for use in the scanning molecular counting method, and additionally, a storage device for storing the calibration curve, a calculation device for calculating the concentration of the luminescent particles in the sample solution on the basis of the calibration curve, and a display 19 for displaying the calculated concentration of the luminescent particles in the sample solution. For this storage device and the calculation device, the computer 18 shown in FIG. 1A can be used.

Figure 11:
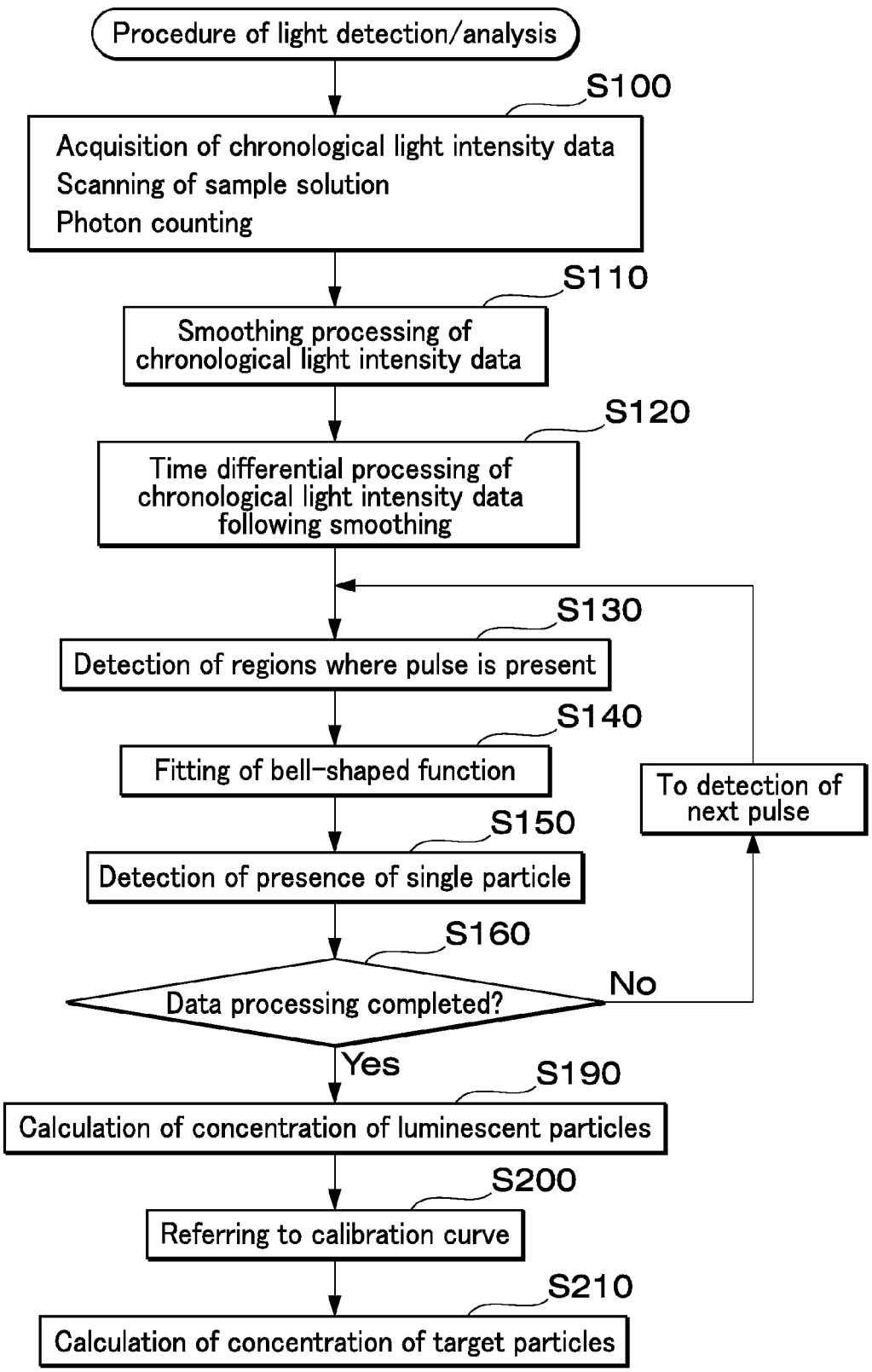
FIG. 11 is a flow chart showing the procedure of processes from the counting of luminescent particles (target particles bound to the luminescent probes) in a sample solution by the scanning molecular counting method, to the measurement of the concentration of the target particles in the sample solution.

In addition, the (b) and (c) can also be performed by the above-mentioned device with a program comprising, as shown in the flow chart shown in FIG. 11, the procedure of processes for counting the particles from the chronological change of the photon counts light intensity measured by the scanning molecular counting method, and additionally, a procedure for, with reference to the calibration curve that approximates the correlation between the concentration (or quantity) of the luminescent particles in the sample solution and the number of the luminescent particles counted from the sample solution, calculating the concentration of the target particles in this solution.

EXAMPLES

Next is a more detailed description of embodiments of the present invention with reference to examples and the like. However, the embodiments of the present invention are not to be limited to the following examples.

Reference Example 1

Experiments to show that it is possible to form a calibration curve on the basis of the measured values of the scanning molecular counting method were performed using a fluorescent dye in different concentrations.

In the measurement, a single molecule fluorescence measuring apparatus MF20 (Olympus Corporation), equipped with the optical system of a confocal fluorescence microscope and a photon counting system was used as the photometric analysis device.

First, sample solutions of ATTO (registered trademark) 633 (manufactured by ATTO-TEC) were prepared with a phosphate buffer solution (including 0.1% Pluronic F-127) so that the concentration would be 100 pM, 10 pM, 1 pM, 100 fM, or 10 fM, respectively. Next, after the optical adjustment of the photometric analysis device, the above-mentioned respective sample solutions were measured to obtain the photon count data chronologically. At this time, 633 nm laser light was used for excitation light and irradiated at 1 mW, and the detected light wavelength was set from 660 to 710 nm using a band pass filter. The speed of moving the position of the light detection region in the sample solution was set to 15 mm/sec, BIN TIME was set to 10 pec, and the measuring time was set to 2 seconds for the samples of 100 pM, 10 pM, and 1 pM, and 20 seconds for the samples of 100 fM and 10 fM (the number of peaks in the graph is a converted value by taking 2-second intervals). Moreover, the measurement was performed five times for each sample, and the average thereof was calculated. After the measurement of the light intensity, from the chronological photon count data acquired on each sample solution, chronological detected light signal data were counted. In the data smoothing by the moving average method, the datum points averaged at once were nine points, and the moving average process was repeated five times. Moreover, in the fitting, the gauss function was fitted to the chronological data by the least square method to determine the peak intensity (in the gauss function), the peak width (full width at half maximum), and the correlation coefficient. Furthermore, in the process of peak judgment, only the peak signals satisfying the following conditions:

20 μsec.<peak width<400 μsec.

peak intensity>1 (photon/10 μsec)

correlation coefficient>0.95 were judged as a light signal corresponding to a molecule as the object of observation. On the other hand, peak signals which did not satisfy the above-mentioned conditions were disregarded as noise, and the number of the signals judged as a light signal corresponding to a molecule as the object of observation was counted as a "number of peaks".

Figure 12:
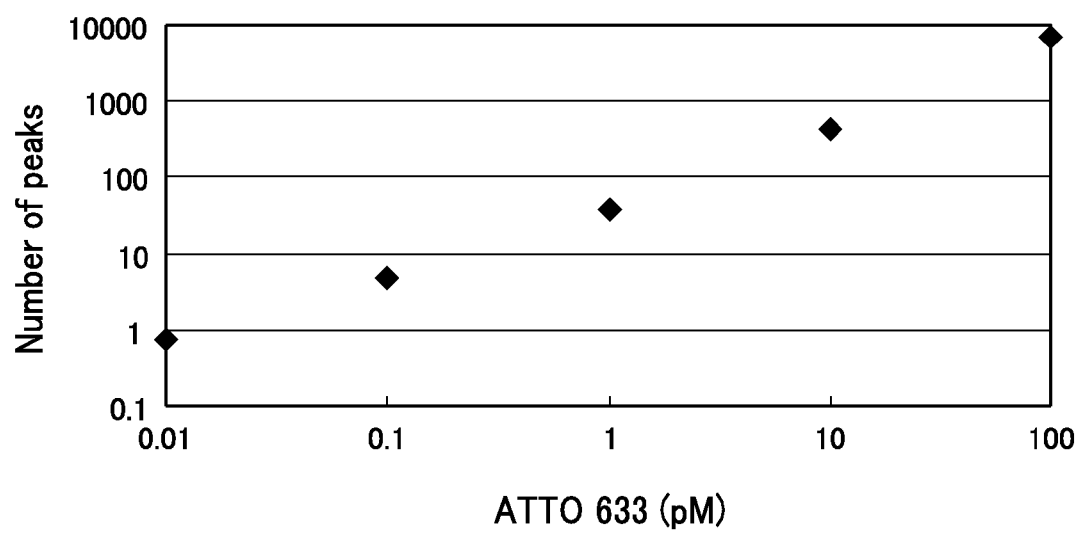
FIG. 12 is a graph showing a calibration curve formed by plotting the counted values of the respective sample solutions wherein the horizontal axis is the concentration of the fluorescent substance ATTO 633 in the sample solution and the vertical axis is the number of peaks (expressed in a logarithmic scale) in Reference Example 1.

FIG. 12 is a graph formed by plotting the counted values of the respective sample solutions wherein the horizontal axis is the concentration of the fluorescent substance ATTO 633 in the sample solution and the vertical axis is the number of peaks (expressed in a logarithmic scale). As a result, it was confirmed that the concentration of ATTO 633 and the number of peaks were in a proportional relation.

Figure 13:
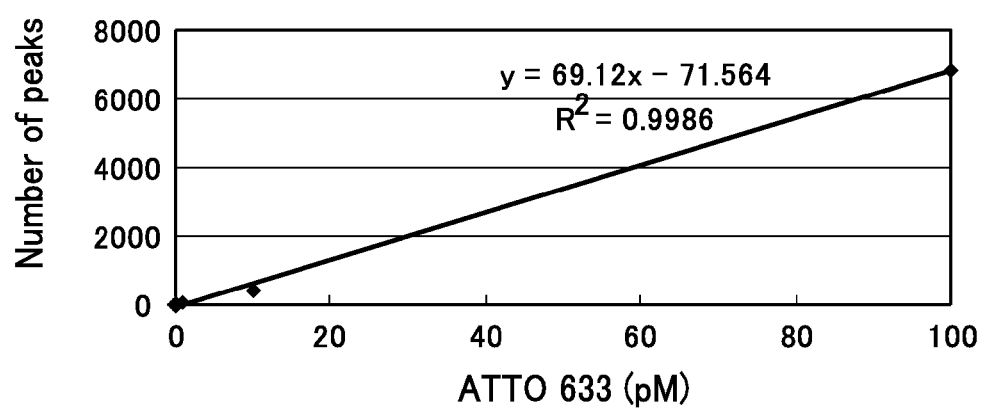
FIG. 13 is a graph showing a calibration curve formed by plotting the counted values of the respective sample solutions wherein the horizontal axis is the concentration of the fluorescent substance ATTO 633 in the sample solution and the vertical axis is the number of peaks (expressed in a normal scale) in Reference Example 1.

Moreover, FIG. 13 is a graph formed by expressing the graph of FIG. 12 in a normal scale. As a result, it was found that there was a strong positive correlation between the concentration of the fluorescent substance ATTO 633 in the solution and the counted number of peaks, and the concentration of a sample having an unknown concentration can be readily determined by using the calibration curve obtained from the respective measured values (shown in FIG. 13). For example, if the number of peaks when measuring a sample having an unknown concentration is 100, the concentration of ATTO 633 of this sample can be calculated to 2.5 pM.

Example 1

A nucleic acid consisting of a base sequence represented by the SEQ NO: 1 was used as the target particle. Hereinunder, in this Example, this nucleic acid is referred to as a target nucleic acid. Moreover, a molecular beacon probe prepared by adding Alexa Fluor 488 to the 5'-end and BHQ-1 to the 3'-end of an oligonucleotide consisting of the base sequence represented by the SEQ NO: 2 was used as the luminescent probe to be bound to this target nucleic acid. These oligonucleotides were synthesized by requesting to Sigma-Genosys Company. The base sequences of the target nucleic acid and the molecular beacon probe are shown in Table 1. In Table 1, the underlined bases in the molecular beacon probe show regions which are hybridized with each other when forming the intramolecular structure.

TABLE 1

| | Base sequence | SEQ NO: |
|---|---|---|
| Target nucleic acid | ATGACTGAATATAAACTTGTGGTAGTTGGAGCTGGT GGCGTAGGCAAGAGTGCCTTGACGATACAGCTAATT CAGAAT | 1 |
| Molecular beacon probe | Alexa488-<u>CCTACGC</u>CACCAGCTC<u>CGTAGG</u>-BHQ1 | 2 |

Standard sample solutions for forming the calibration curve were prepared by dissolving the above-mentioned molecular beacon probe and the target nucleic acid so that the concentration of the molecular beacon probe would be 100 pM and the concentration of the target nucleic acid would be 100 nM, 10 nM, 1 nM, 100 pM, or 10 pM, in a Tris buffer solution (10 mM Tris-HCl, 1 mM EDTA, 400 mM NaCl, and pH 8.0).

The respective standard sample solutions were heated at 95° C. for 5 minutes to effect denaturation, and then were gradually cooled down to 20° C. so as to thereby form an associated body in which the target nucleic acid and the molecular beacon probe are bound. Concretely, the cooling speed was set to 0.1° C./sec, and a cooling treatment consisting of 90° C. for 5 minutes, 80° C. for 10 minutes, 70° C. for 10 minutes, 60° C. for 10 minutes, 50° C. for 10 minutes, 40° C. for 10 minutes, and 30° C. for 10 minutes was performed.

The number of molecules of the associated bodies in each standard sample solution after the cooling treatment was counted by the scanning molecular counting method. Concretely, in the measurement, a single molecule fluorescence measuring apparatus MF20 (Olympus Corporation), equipped with the optical system of a confocal fluorescence microscope and a photon counting system was used as the photometric analysis device, to obtain the photon count data in chronological of the above-mentioned respective standard sample solutions. At this time, 488 nm laser light was used for excitation light and irradiated at 300 μW, and the detected light wavelength was set from 510 to 560 nm using a band pass filter. The speed of moving the position of the light detection region in the standard sample solution was set to 15 mm/sec, BIN TIME was set to 10 μsec, and the measuring time was set to 2 seconds. Moreover, the measurement was performed five times for each sample, and the average and the standard deviation thereof were calculated. After the measurement of the light intensity, from the chronological photon count data acquired on each standard sample solution, chronological detected light signal data were counted. In the data smoothing by the moving average method, the datum points averaged at once were nine points, and the moving average process was repeated five times. Moreover, in the fitting, the gauss function was fitted to the chronological data by the least square method to determine the peak intensity (in the gauss function), the peak width (full width at half maximum), and the correlation coefficient. Furthermore, in the process of peak judgment, only the peak signals satisfying the following conditions:

20 μsec.<peak width<400 μsec.

peak intensity>1 (photon/10 μsec.)

correlation coefficient>0.95 were judged as a light signal corresponding to a nucleic acid as the object of observation, while peak signals which did not satisfy the above-mentioned conditions were disregarded as noise, and the number of the signals judged as a light signal corresponding to a nucleic acid as the object of observation was counted as a "number of peaks."

Figure 14:
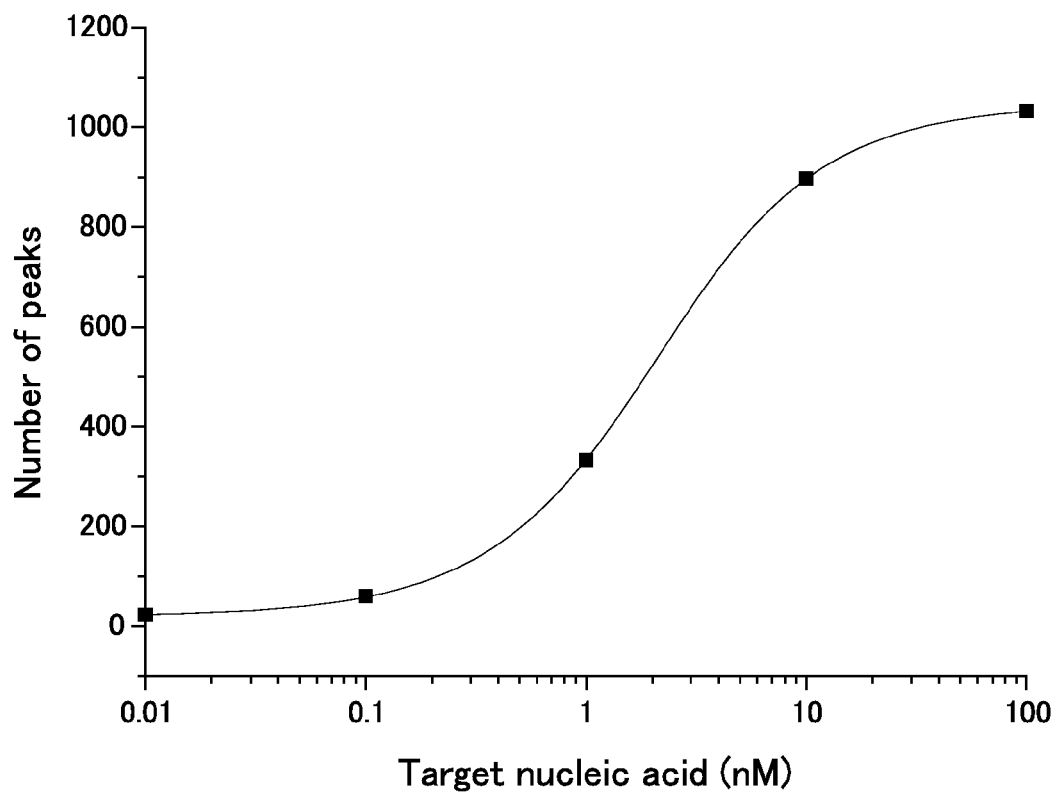
FIG. 14 is a graph showing a calibration curve formed by plotting the counted values of the respective standard sample solutions wherein the horizontal axis is the concentration of the target nucleic acid in the standard sample solution and the vertical axis is the number of peaks in Example 1.
Figure 15:
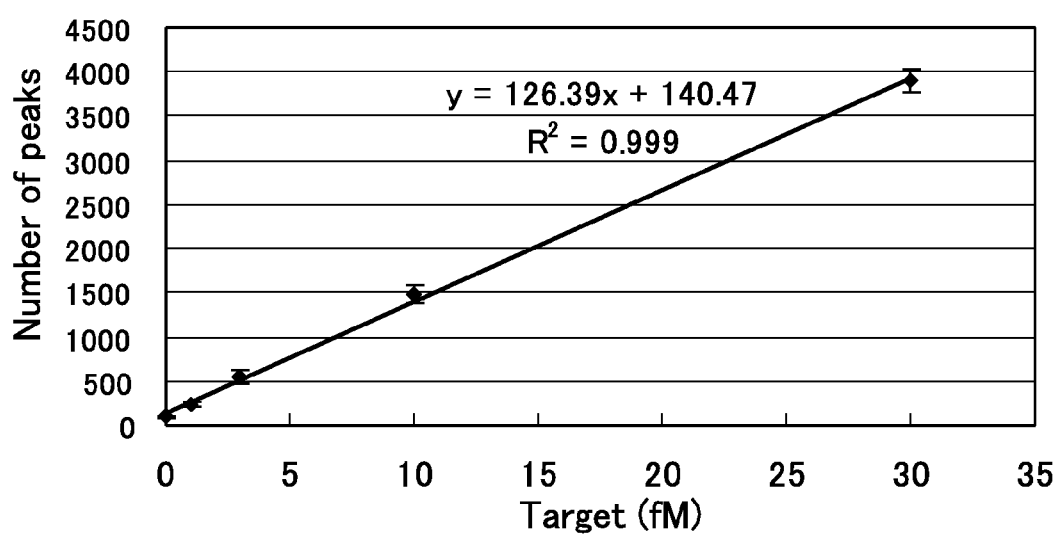
FIG. 15 is a graph showing a calibration curve formed by plotting the counted values of the respective standard sample solutions wherein the horizontal axis is the concentration of the target nucleic acid in the standard sample solution and the vertical axis is the number of peaks in Example 2.

FIG. 14 is a graph formed by plotting the counted obtained values from the respective standard sample solutions wherein the horizontal axis is the concentration of the target nucleic acid in the standard sample solution and the vertical axis is the number of peaks. As a result, it was confirmed that the number of peaks was changed dependently on the concentration of the target nucleic acid.

The approximate curve of the respective plots was used as the calibration curve to obtain the target nucleic acid concentration of a sample solution having an unknown concentration. Concretely, similarly to the above-mentioned standard sample solution, the molecular beacon probe was added to the unknown sample solution to form an associated body with the molecular beacon probe. Then, the measurement was performed using the photometric analysis device, and the number of peaks was calculated. As a result, the number of peaks counted from this unknown sample solution was 421. By referring to the calibration curve shown in FIG. 13, the target nucleic acid concentration of this unknown sample solution was able to be calculated to 1.4 nM.

Example 2

A nucleic acid consisting of a base sequence represented by the SEQ NO: 3 was used as the target particle. Hereinunder, in this Example, the nucleic acid is referred to as a target nucleic acid 2. Moreover, a fluorescence probe was used as the luminescent probe, a biotin probe was used as the separation probe, and magnetic beads coated with streptavidin were used as the solid-phase carrier.

In addition, a fluorescence probe prepared by adding ATTO 647N to the 5'-end of an oligonucleotide consisting of the base sequence represented by the SEQ NO: 4 was used as the luminescent probe to be bound to this target nucleic acid 2. Furthermore, a biotin probe prepared by adding biotin to the 3'-end of an oligonucleotide consisting of the base sequence represented by the SEQ NO: 5 was used as the probe to be bound to this target nucleic acid 2. These oligonucleotides were synthesized by requesting to Sigma-Genosys Company. The base sequences of the target nucleic acid 2, the fluorescence probe, and the biotin probe are shown in Table 2.

TABLE 2

| | Base sequence | SEQ NO: |
|---|---|---|
| Target nucleic acid 2 | GACTGAATATAAACTTGTGGAGCCTGGGAAAG TCCCCTCAACT | 3 |
| Luminescent probe | ATTO 647N-AGTTGAGGGGACTTTCCCAGGC | 4 |
| Biotin probe | CCACAAGTTTATATTCAGTC-Biotin | 5 |

Sample solutions (1004) were prepared so that the concentration of the target nucleic acid 2 would be 30 fM, 10 fM, 3 fM, or 1 fM, the concentration of the fluorescence probe would be 20 pM, the concentration of the biotin probe would be 200 pM, and the concentration of the poly(deoxyinosinic-deoxycytidylic) acid (Sigma-Aldrich Corporation) would be 0.1 U/mL (1 U is a quantity at which the absorbance of 260 nm is 1.0 in water (optical path length of 1 cm)) in a Tris buffer solution (10 mM Tris-HCl, 400 mM NaCl, and 0.05% Triton X-100). A sample containing no target nucleic acid 2 was also prepared. These sample solutions were heated at 95° C. for 5 minutes, and then cooled down to 25° C. at a speed of 0.1° C./min. 14 of 0.1% BSA (bovine serum albumin) was added thereto, and the mixture was reacted with 10 μg of streptavidin-coated magnetic beads (Invitrogen, Cat. No. 650) at 25° C. for 90 minutes under shaking. Subsequently, the solution was washed three times with 500 μL of a washing buffer solution (10 mM Tris-HCl, 400 mM NaCl, and 0.05% Triton X-100) using a magnet, then 100 μL of an elution buffer solution (10 mM Tris-HCl and 0.05% Triton X-100) was added thereto, and the mixture was left standing at 50° C. for 5 minutes. The magnetic beads were gathered by a magnet, and then the supernatant was collected. These were used as the standard sample solutions and measured by the scanning molecular counting method.

In the measurement, a single molecule fluorescence measuring apparatus MF20 (Olympus Corporation), equipped with the optical system of a confocal fluorescence microscope and a photon counting system was used as the photometric analysis device, to obtain the photon count data in chronological of the above-mentioned supernatants. At this time, 642 nm laser light was used for excitation light and irradiated at 1 mW, and the detected light wavelength was set from 660 to 710 nm using a band pass filter. The speed of moving the position of the light detection region in the sample solution was set to 67.5 mm/sec, BIN TIME was set to 10 μsec, and the measuring time was set to 600 seconds. Moreover, the measurement was performed five times for each supernatant, and the average and the standard deviation thereof were calculated. After the measurement of the light intensity, from the chronological photon count data acquired on each supernatant, chronological detected light signal data were counted. In the data smoothing by the moving average method, the datum points averaged at once were eleven points, and the moving average process was repeated five times. Moreover, in the fitting, the gauss function was fitted to the chronological data by the least square method to determine the peak intensity (in the gauss function), the peak width (full width at half maximum), and the correlation coefficient. Furthermore, in the process of peak judgment, only the peak signals satisfying the following conditions:

20 μsec.<peak width<400 μsec.

peak intensity>1 (photon/10 μsec)

correlation coefficient>0.90 were judged as a light signal corresponding to a fluorescence probe, while peak signals which did not satisfy the above-mentioned conditions were disregarded as noise, and the number of the signals judged as a light signal corresponding to a fluorescence probe was counted as a "number of peaks."

FIG. 14 is a graph formed by plotting the counted values obtained from the respective standard sample solutions wherein the horizontal axis is the concentration of the target nucleic acid 2 in the standard sample solution and the vertical axis is the number of peaks. As a result, it was confirmed that the number of peaks was changed dependently on the concentration of the target nucleic acid 2.

The approximate curve of the respective plots was used as the calibration curve to obtain the target nucleic acid concentration of a sample solution having an unknown concentration. Concretely, similarly to the above-mentioned standard sample solution, a sample for the measurement was produced for the sample solution having an unknown concentration. Then, the measurement was performed using the photometric analysis device, and the number of peaks was calculated. As a result, the number of peaks counted from this sample solution having an unknown concentration was 724. By referring to the calibration curve shown in FIG. 14, the target nucleic acid concentration of this sample solution having an unknown concentration was able to be calculated to 4.6 fM.

INDUSTRIAL APPLICABILITY

With the quantitative determination method for target particles mentioned above, the concentration of target particles which exist only at a very low concentration in a sample solution can be quantitatively measured by the scanning molecular counting method. Therefore, this quantitative determination method is applicable to the fields of analysis/test and the like of a sample in which the concentration of a substance as the object of analysis is very small, such as a clinical analyte, or the like.

BRIEF DESCRIPTION OF THE REFERENCE SYMBOLS

F: Fluorescent dye (luminescent probes)
T: Particle as the object (target particles)
1: Photometric analysis device (confocal microscope)
2: Light source
3: Single mode optical fiber
4: Collimating lens
5: Dichroic mirror
6, 7, and 11: Reflective mirror
8: Object lens
9: Micro plate
10: Well (sample solution container)
12: Condenser lens
13: Pinhole
14: Barrier filter
15: Multi-mode optical fiber
16: Photodetector
17: Mirror deflector (light detection region mover)
17a: Stage position changing apparatus
18: Computer
19: Display

---

The invention claimed is:

1. A method for quantifying target particles which are dispersed and moving at random in a sample solution, the method comprising:
   (a) preparing a sample solution containing the target particles and luminescent probes to be bound to the target particles, and binding the target particles and the luminescent probes in the sample solution;
   (b) moving a position of a light detection region of an optical system in the sample solution with use of an optical system of a confocal microscope or a multiphoton microscope, and detecting a light signal emitted from the luminescent probes in the light detection region while moving the position of the light detection region of the optical system in the sample solution, and individually detecting the target particle directly or indirectly; and
   (c) counting, using a processor, the number of the target particles detected in the (b) and calculating, using the processor, the concentration of the target particles in the sample solution from the number of the counted target particles on the basis of a calibration curve that approximates the correlation between the concentration or quantity of the target particles in the sample solution and the number of the target particles.

2. The method for quantifying target particles according to claim 1, wherein
   the position of the light detection region is moved at a predetermined speed, in the moving step.

3. The method for quantifying target particles according to claim 1, wherein
   the position of the light detection region is moved at a speed higher than the speed of diffusional movement of either quicker ones of the luminescent probes or the target particles bound to the luminescent probes, in the moving step.

4. The method for quantifying target particles according to claim 1, wherein
   it is detected that the luminescent probe or the target particle bound to the luminescent probe has entered the light detection region, based on the shape of the chronological detected light signal, in the detection step.

5. The method for quantifying target particles according to claim 1, wherein:
   the luminescent probe has an energy donor site and an energy acceptor site, which produce a fluorescence energy transfer phenomenon when these sites are close to each other;
   the distance between the energy donor site and the energy acceptor site is different between a binding state where the luminescent probe is bound to the target particle and a non-binding state where the luminescent probe is not bound to the target particle; and
   an emission characteristic of light emitted from the luminescent probe is different between the binding state and the non-binding state.

6. The method for quantifying target particles according to claim 1, wherein:
   the target particle is a nucleic acid; and
   the luminescent probe is a single stranded nucleic acid which is specifically hybridizable with the target particle, and which is bound with at least either one of a fluorescent substance serving as an energy donor and a substance serving as an energy acceptor in a fluorescence energy transfer phenomenon.

7. The method for quantifying target particles according to claim 1, further comprising:
(d) separating a luminescent probe which is not bound to the target particle from the sample solution, and collecting a complex including the target particle and the luminescent probe, after the (a).

8. The method for quantifying target particles according to claim 7, further comprising:
(e) dissociating the luminescent probe from the complex having been collected in the (d), thereafter separating the free luminescent probe and the target particle from each other, and collecting them.

9. A photometric analysis device for detecting light from luminescent particles dispersed and moving at random in a sample solution, with use of an optical system of a confocal microscope or a multiphoton microscope, the device comprising:
a light detection region mover for moving a position of a light detection region of the optical system in the sample solution by changing an optical path of the optical system;
a light detector for detecting light from the luminescent particle in the light detection region;
a signal processor for individually detecting a light signal of the light emitted from respective ones of the luminescent particles detected in the light detector while moving the position of the light detection region in the sample solution, and counting the number of the luminescent particles detected during the moving of the position of the light detection region by counting the number of the individually detected light signals from the luminescent particle;
a storage for storing a calibration curve that approximates the correlation between the concentration or quantity of the luminescent particles in the sample solution and the number of the luminescent particles counted from the sample solution;
a concentration calculator for, on the basis of the calibration curve, calculating the concentration of the luminescent particles in the sample solution from the number of the luminescent particles counted in the signal processor; and
a display for displaying the concentration of the luminescent particles in the sample solution calculated by the concentration calculator.

10. The device according to claim 9, wherein
the light detection region mover moves the position of the light detection region at a predetermined speed.

11. The device according to claim 9, wherein
the light detection region mover moves the position of the light detection region at a speed higher than the speed of diffusional movement of the luminescent particle.

12. The device according to claim 9, wherein
the signal processor detects that one of the luminescent particles has entered the light detection region, based on the shape of the chronological detected light signal in the light detector.

13. The device according to claim 12, wherein
the signal processor detects that one of the luminescent particles has entered the light detection region, when the light signal having an intensity greater than a predetermined threshold value is detected.

14. The device according to claim 9, wherein
the signal processor determines the number density or concentration of the luminescent particles in the sample solution, on the basis of the number of the detected luminescent particles.

15. A non-transitory computer readable storage device having a computer program product including programmed instructions for photometric analysis of detecting light from a luminescent particle dispersed and moving at random in a sample solution, with use of an optical system of a confocal microscope or a multiphoton microscope, the programmed instructions causing a computer to perform the steps comprising:
changing the optical path of the optical system, so as to move a position of a light detection region of the optical system in the sample solution;
detecting the light from the luminescent particle in the light detection region, while moving the position of the light detection region in the sample solution;
individually detecting a light signal of the light emitted from respective ones of the detected luminescent particle;
counting the number of the luminescent particles detected during the moving of the position of the light detection region by counting the number of the individually detected light signals of the light from the luminescent particles; and
calculating the concentration of the target particles in the sample solution from the counted number of the luminescent particles on the basis of a calibration curve that approximates the correlation between the concentration or quantity of the luminescent particles in the sample solution and the number of the luminescent particles counted from the sample solution.

16. The non-transitory computer readable storage device according to claim 15, wherein
the position of the light detection region is moved at a predetermined speed, in the changing step.

17. The non-transitory computer readable storage device according to claim 15, wherein
the position of the light detection region is moved at a speed higher than the speed of diffusional movement of the luminescent particle, in the changing step.

18. The non-transitory computer readable storage device according to claim 15, wherein
it is detected that one of the luminescent particles has entered the light detection region, based on the shape of the chronological detected light signal, in the light signal detection step.

19. The non-transitory computer readable storage device according to claim 15, wherein
it is detected that one of the luminescent particles has entered the light detection region, when a light signal having an intensity greater than a predetermined threshold value is detected, in the light signal detection step.

20. The non-transitory computer readable storage device according to claim 15, further comprising a procedure for determining the number density or concentration of the luminescent particles in the sample solution, on the basis of the number of the detected luminescent particles.

* * * * *

SEQUENCE LISTING

```
<160> NUMBER OF SEQ ID NOS: 5

<210> SEQ ID NO 1
<211> LENGTH: 78
<212> TYPE: DNA
<213> ORGANISM: Artificial Sequence
<220> FEATURE:
<223> OTHER INFORMATION: Description of Artificial Sequence: Target
      oligonucleotide

<400> SEQUENCE: 1
atgactgaat ataaacttgt ggtagttgga gctggtggcg taggcaagag tgccttgacg     60
atacagctaa ttcagaat                                                  78

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Molecular
      beacon probe

<400> SEQUENCE: 2
cctacgccac cagctccgta gg                                             22
```

```
<210> SEQ ID NO 3
<211> LENGTH: 43
<212> TYPE: DNA
<213> ORGANISM: Artificial Sequence
<220> FEATURE:
<223> OTHER INFORMATION: Description of Artificial Sequence: Target
      oligonucleotide 2

<400> SEQUENCE: 3
gactgaatat aaacttgtgg agcctgggaa agtcccctca act              43

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:
      Fluorescence probe

<400> SEQUENCE: 4
agttgagggg actttcccag gc                                     22

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Biotin
      probe

<400> SEQUENCE: 5
ccacaagttt atattcagtc                                        20
```